(12) United States Patent
Ikeda et al.

(10) Patent No.: US 6,503,451 B2
(45) Date of Patent: Jan. 7, 2003

(54) OXYGENATOR OF HOLLOW FIBER MEMBRANE TYPE

(75) Inventors: Tomohiko Ikeda, Saitama (JP); Kazuhiko Takeuchi, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 40 days.

(21) Appl. No.: 09/735,619

(22) Filed: Dec. 14, 2000

(65) Prior Publication Data

US 2002/0039543 A1 Apr. 4, 2002

(30) Foreign Application Priority Data

Dec. 15, 1999 (JP) .......................................... 11-356195

(51) Int. Cl.$^7$ ............................. B65B 1/04; B01D 11/00
(52) U.S. Cl. ......................................... 422/45; 604/6.14
(58) Field of Search ....................... 422/45–48; 604/6.14

(56) References Cited

U.S. PATENT DOCUMENTS

| | | | |
|---|---|---|---|
| 4,207,192 A | | 6/1980 | Coplan et al. |
| 5,312,589 A | * | 5/1994 | Reeder et al. ................. 422/45 |
| 5,346,621 A | | 9/1994 | Haworth et al. |
| 5,462,619 A | | 10/1995 | Haworth et al. |
| 5,762,868 A | * | 6/1998 | Leonard ....................... 422/46 |
| 5,762,869 A | * | 6/1998 | White et al. ................... 422/45 |

FOREIGN PATENT DOCUMENTS

| | | |
|---|---|---|
| EP | 0 264 696 A2 | 4/1988 |
| EP | 0 895 786 A1 | 2/1999 |
| JP | 56-87405 A | 7/1981 |
| JP | 7-509171 | 10/1995 |
| WO | WO 97/08933 A2 | 3/1997 |

* cited by examiner

Primary Examiner—Steven O. Douglas
(74) Attorney, Agent, or Firm—Burns, Doane, Swecker Mathis, LLP

(57) ABSTRACT

An oxygenator of hollow fiber membrane type of the present invention includes a cylindrical core; a cylindrical hollow fiber membrane bundle consisting of a plurality of gas-exchange hollow fiber membranes wound on an outer surface of the cylindrical core; a housing accommodating the cylindrical hollow fiber membrane bundle; a gas inlet portion and a gas outlet portion both communicating with the interior of the hollow fiber membrane; and a blood inlet portion and a blood outlet portion communicating with the outside of the hollow fiber membrane and the interior of the housing. The hollow fiber membranes of the cylindrical hollow fiber membrane bundle wound on cylindrical core are multi-layered on the outer surface thereof. Each hollow fiber membrane layer has cross portions of the hollow fiber membranes in the neighborhood of the center of the cylindrical core in a longitudinal direction thereof. Positions of the cross portions of each of the respective hollow fiber membrane layers are differentiated from one another to prevent contact between the cross portions of the hollow fiber membrane layers laminated on each other.

13 Claims, 15 Drawing Sheets

OXYGENATOR OF HOLLOW FIBER MEMBRANE TYPE

BACKGROUND OF THE INVENTION

The present invention relates to an oxygenator of hollow fiber membrane type for removing carbon dioxide contained in blood and adding oxygen to the blood in an extracorporeal blood circulation.

In recent years, there is proposed (for example, Japanese Patent Application Laid-Open No. 7-509171) an oxygenator using a hollow fiber membrane bundle produced by winding hollow fiber membranes spirally on a hollow cylindrical core. The hollow fiber membrane bundle of this type has cross portions where the wound hollow fiber membranes cross.

Cross Portions of the wound hollow fiber membranes and annular portions formed of the cross portions layered one on the other are formed by controlling a rotating means for rotating the hollow cylindrical core and a winder for weaving the hollow fiber membranes under a predetermined condition. A short circuit of blood may be formed due to the annular portions formed of the cross portions layered one on the other, which causes reduction of gas exchange performance.

Therefore, in providing an oxygenator of hollow fiber membrane type using a hollow fiber membrane bundle produced by winding hollow fiber membranes spirally on a hollow cylindrical core and having annular portions formed of cross portions of the hollow fiber membranes layered one on the other, the oxygenator is intended to hardly generate a cross portion-caused short-circuited path of blood and have a high degree of gas exchange performance.

SUMMARY OF THE INVENTION

The object of this invention is to provide an oxygenator of hollow fiber membrane type that comprises a cylindrical core; a cylindrical hollow fiber membrane bundle consisting of a plurality of gas-exchange hollow fiber membranes wound on an outer surface of said cylindrical core; a housing accommodating said cylindrical hollow fiber membrane bundle; a gas inlet portion and a gas outlet portion both communicating with the interior of said hollow fiber membranes; and a blood inlet portion and a blood outlet portion communicating with the outside of said hollow fiber membranes and the interior of said housing, wherein said hollow fiber membranes of said cylindrical hollow fiber membrane bundle are multi-layered on the outer surface of said cylindrical core; each hollow fiber membrane layer has cross portions of the hollow fiber membranes in the neighborhood of a center of said cylindrical core in the longitudinal direction thereof and positions of said cross portions of each of said respective hollow fiber membrane layers are differentiated from one another to prevent contact between said cross portions of said hollow fiber membrane layers laminated on each other or to prevent contact between said cross portion of another hollow fiber membrane layer and cross portions of two hollow fiber membrane layers laminated on each other.

BRIEF DESCRIPTION OF THE DRAWINGS

The foregoing and further objects, features and advantages of the present invention will become apparent from the following description of preferred embodiments with reference to the accompanying drawings, wherein like numerals are used to represent like elements and wherein.

DETAILED DESCRIPTION OF PREFERRED EMBODIMENTS

Figure 1:
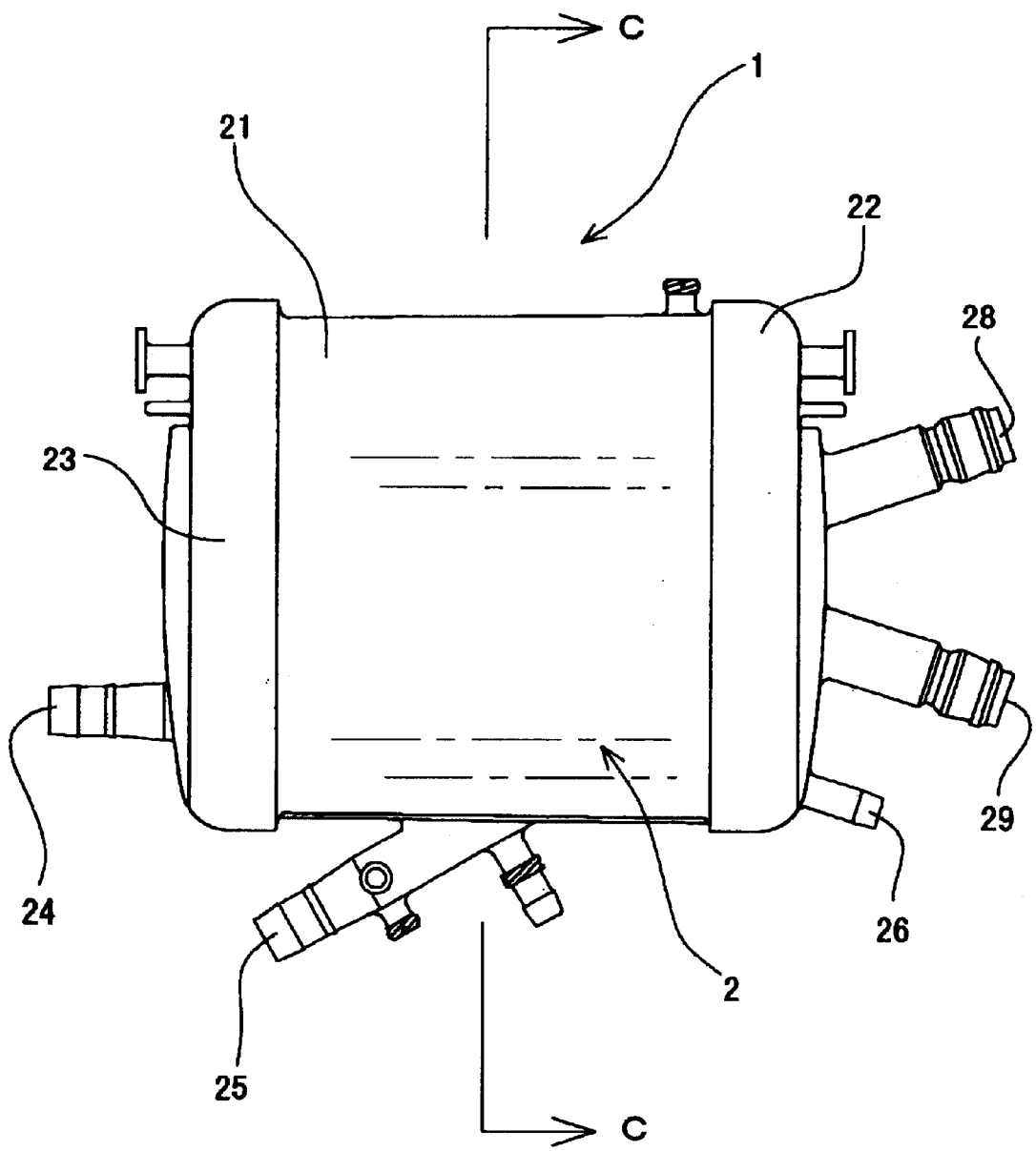
FIG. 1 is a front view showing an oxygenator of hollow fiber membrane type according to a first embodiment of the present invention.
Figure 2:
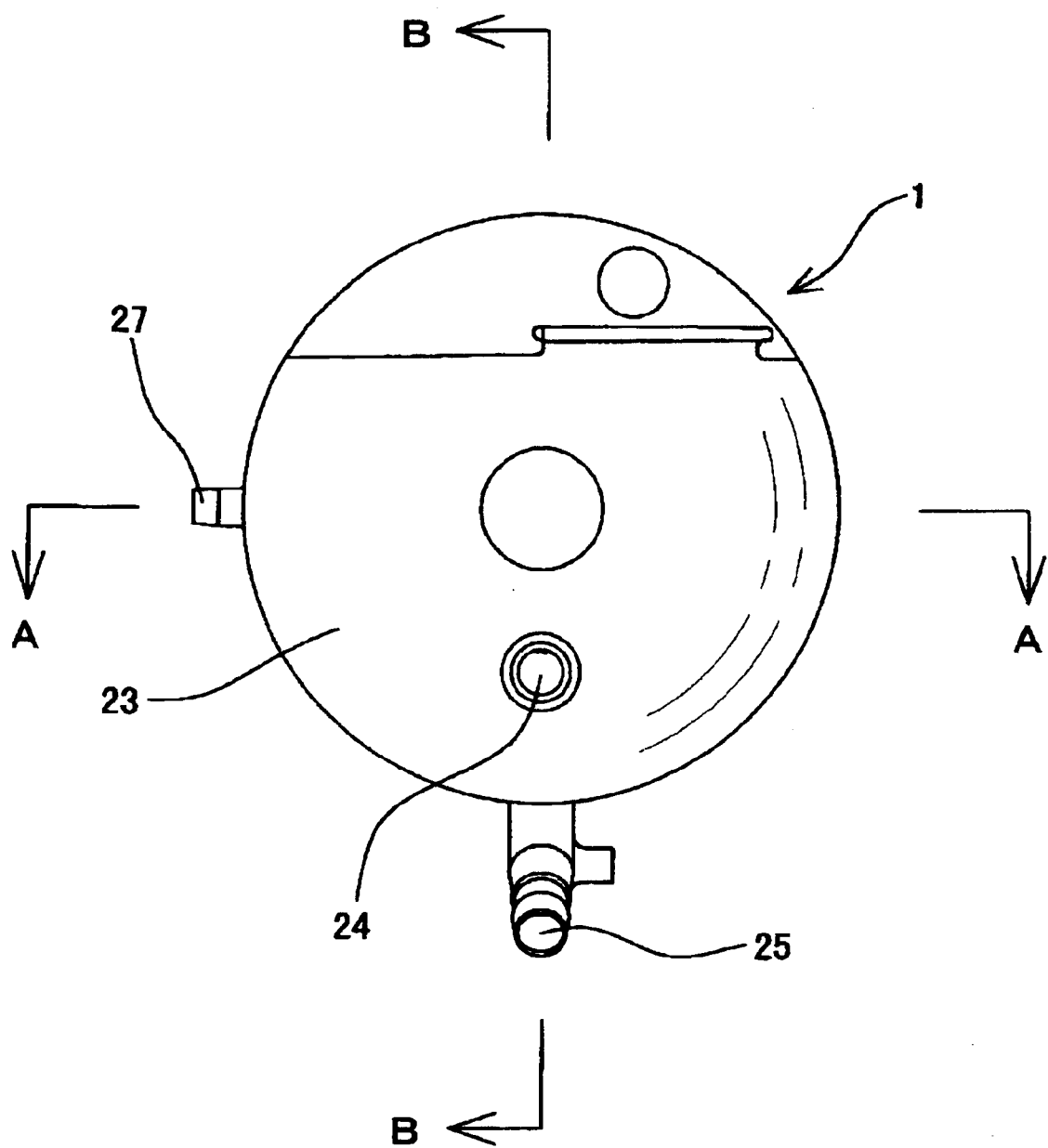
FIG. 2 is a left side view showing the oxygenator of hollow fiber membrane type shown in FIG. 1.
Figure 3:
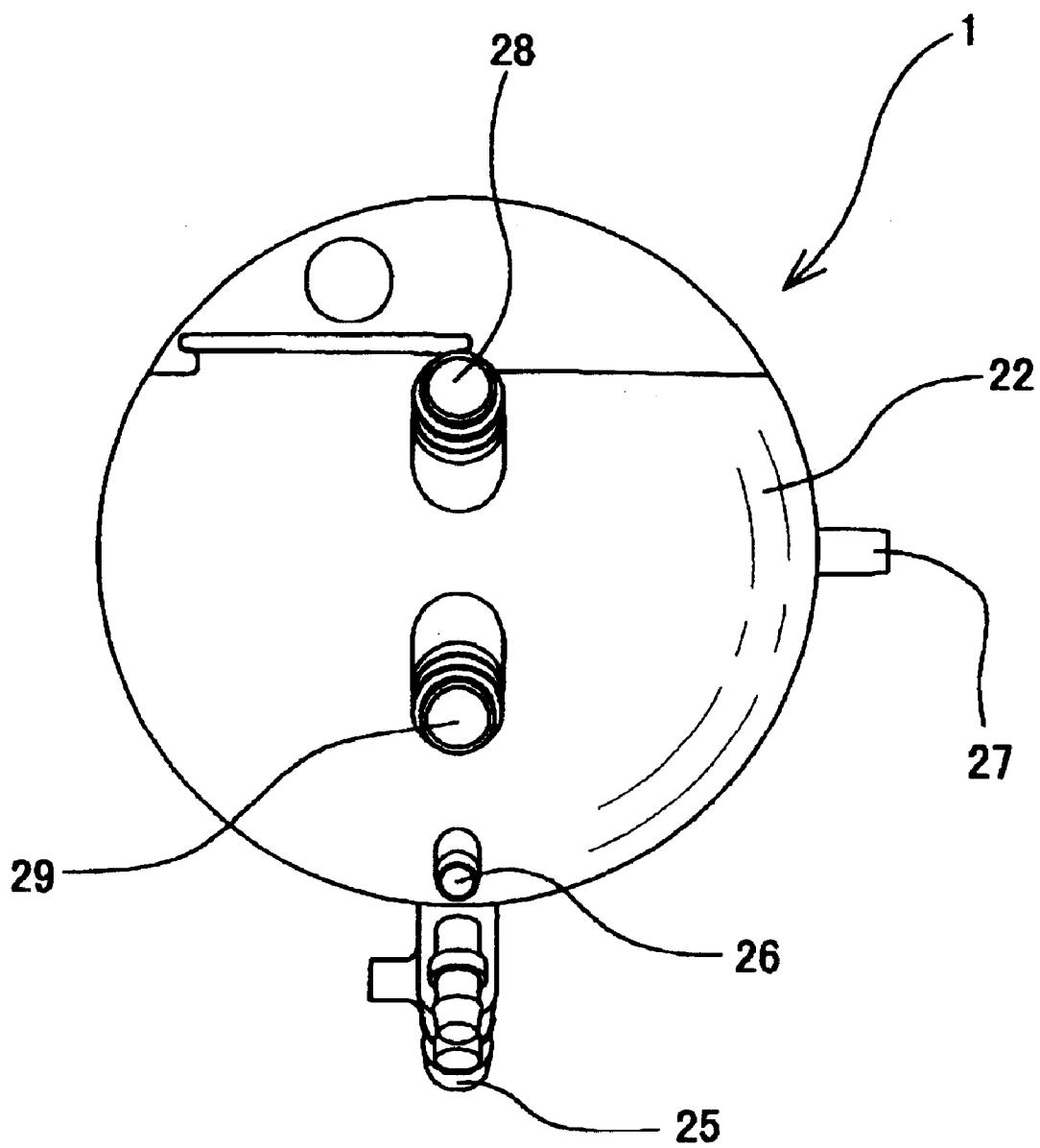
FIG. 3 is a right side view showing the oxygenator of hollow fiber membrane type shown in FIG. 1.

The oxygenator of hollow fiber membrane type of the present invention will be described below with reference to the drawings.

An oxygenator 1 of hollow fiber membrane type of the present invention includes a cylindrical core 5; a cylindrical hollow fiber membrane bundle 3 consisting of a plurality of gas-exchange hollow fiber membranes 3a wound on an outer surface of the cylindrical core 5; a housing accommodating the cylindrical hollow fiber membrane bundle 3; a gas inlet portion and a gas outlet portion both communicating with the interior of the hollow fiber membrane 3a; and a blood inlet portion and a blood outlet portion communicating with the outside of the hollow fiber membrane 3a and the interior of the housing. The hollow fiber membranes of the cylindrical hollow fiber membrane bundle wound on cylindrical core 5 are multi-layered on the outer surface thereof, in other words, spirally layered thereon. That is, the hollow fiber membrane 3a is reeled on the cylindrical core 5. The hollow fiber membranes form a hollow fiber membrane layer reeled on the cylindrical core 5. Each hollow fiber membrane layer has cross portions 3b of the hollow fiber membranes 3a in the neighborhood of the center of the cylindrical core 5 in a longitudinal direction thereof.

Positions of the cross portions 3b of each of the respective hollow fiber membrane layers are differentiated from one another to prevent contact between the cross portions 3b of the hollow fiber membrane layers laminated on each other. Also, Positions of the cross portions of each of the respective hollow fiber membrane layers may be differentiated from one another to prevent contact between the cross portion of one or more of the hollow fiber membrane layers and the cross portions of the hollow fiber membrane layers laminated on each other. Also, positions of the cross portions of each of the respective hollow fiber membrane layers may be differentiated from one another to prevent contact between said cross portion of another hollow fiber membrane layer and cross portions of two hollow fiber membrane layers laminated on each other.

The oxygenator 1 of hollow fiber membrane type of the embodiment has a housing 2; an oxygenating portion accommodated in the housing 2; and a cylindrical heat exchanging part accommodated in the oxygenating portion. The oxygenator is of hollow fiber membrane type containing a heat exchange function.

The oxygenator 1 of hollow fiber membrane type includes a oxygenating portion consisting the cylindrical core 5 and the cylindrical hollow fiber membrane bundle 3 consisting of a plurality of the gasexchange hollow fiber membranes 3a wound on the outer surface of the cylindrical core 5; the cylindrical heat exchanging part accommodated in the cylindrical core 5; and the housing 2 accommodating the oxygenating portion and the cylindrical heat exchanging part.

The cylindrical core 5 includes a groove 51 forming a blood duct between the outer surface of the cylindrical core 5 and the inner surface of the cylindrical hollow fiber membrane bundle 3; and a blood-circulating opening 52 allowing communication between the groove 51 and a first blood chamber 11 formed between the cylindrical core 5 and the cylindrical heat exchanging part. The oxygenator 1 includes a blood inlet port 24 communicating with the first blood chamber 11 formed between the cylindrical core 5 and the cylindrical heat exchanging part; and a blood outlet port 25 communicating with a second blood chamber 12 formed between the outer surface of the cylindrical hollow fiber membrane and the inner surface of the housing 2.

Figure 10:
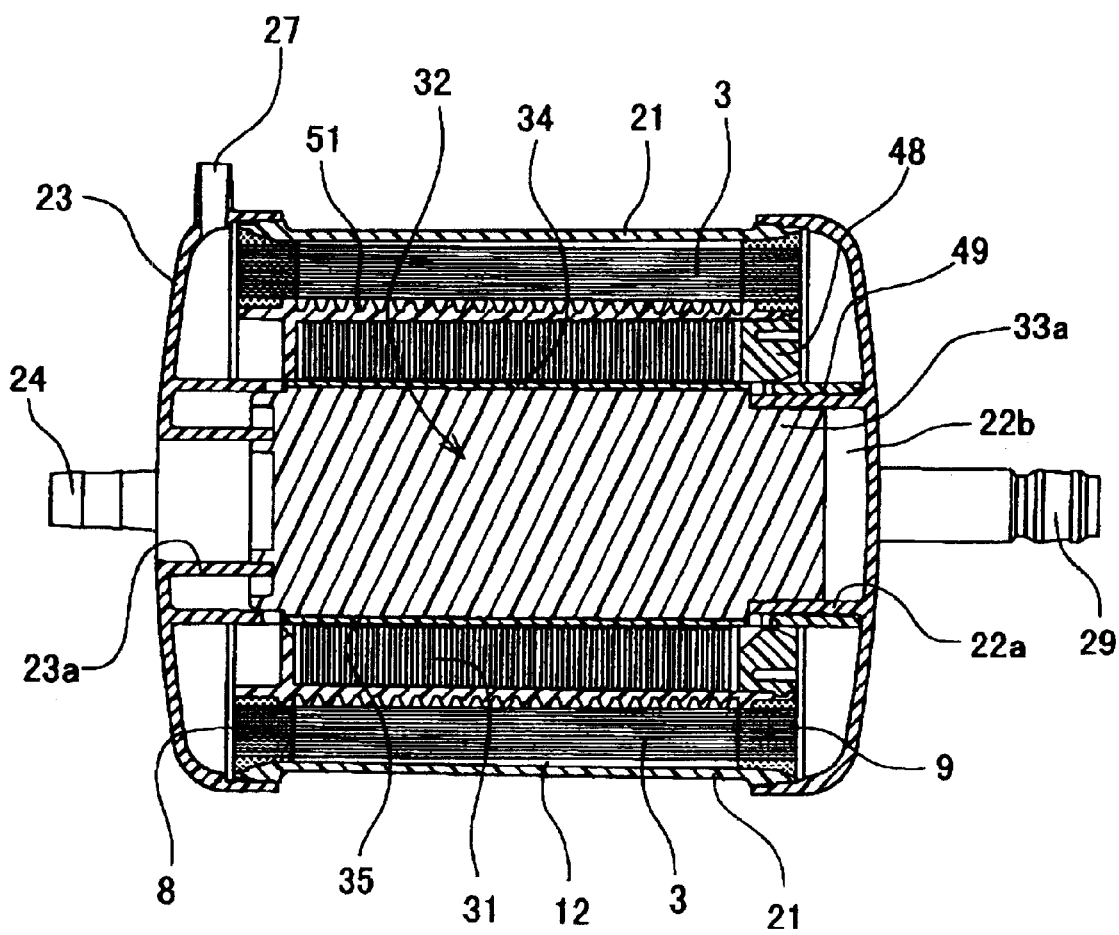
FIG. 10 is a sectional view taken along a line A—A of FIG. 2.
Figure 12:
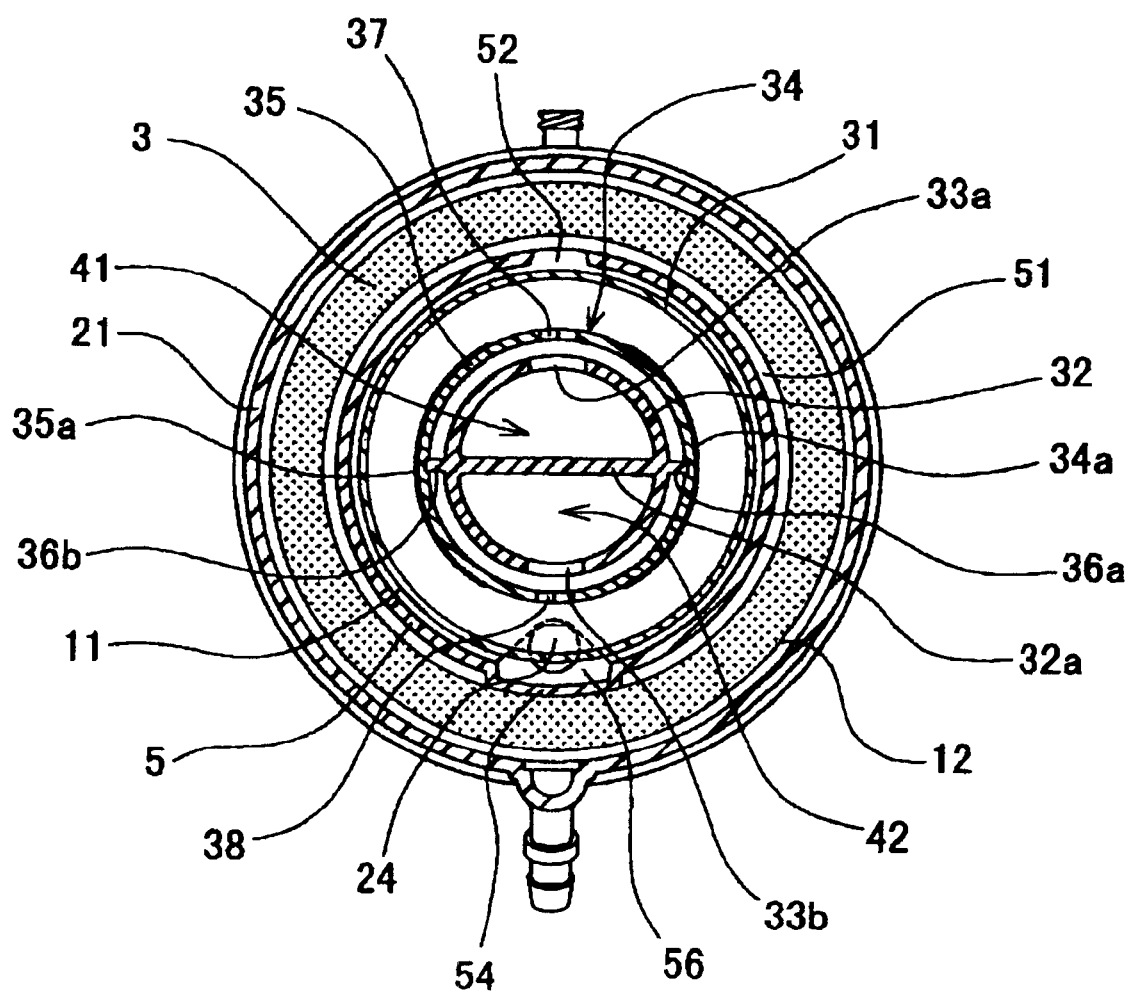
FIG. 12 is a sectional view taken along a line C—C of FIG. 1.

As shown in FIGS. 10 and 12, in the oxygenator 1 of hollow fiber membrane type of the embodiment, from the outside, there are concentrically disposed or formed in the order of a cylindrical body 21 of the housing 2, the second blood chamber 12, the hollow fiber membrane bundle 3, the cylindrical core 5 having the groove 51, the first blood chamber 11, the cylindrical heat exchanger 31, the cylindrical prevention portion 34, 35 for preventing deformation of the heat exchanger and the cylindrical heating medium chamber-forming member 32.

Figure 11:
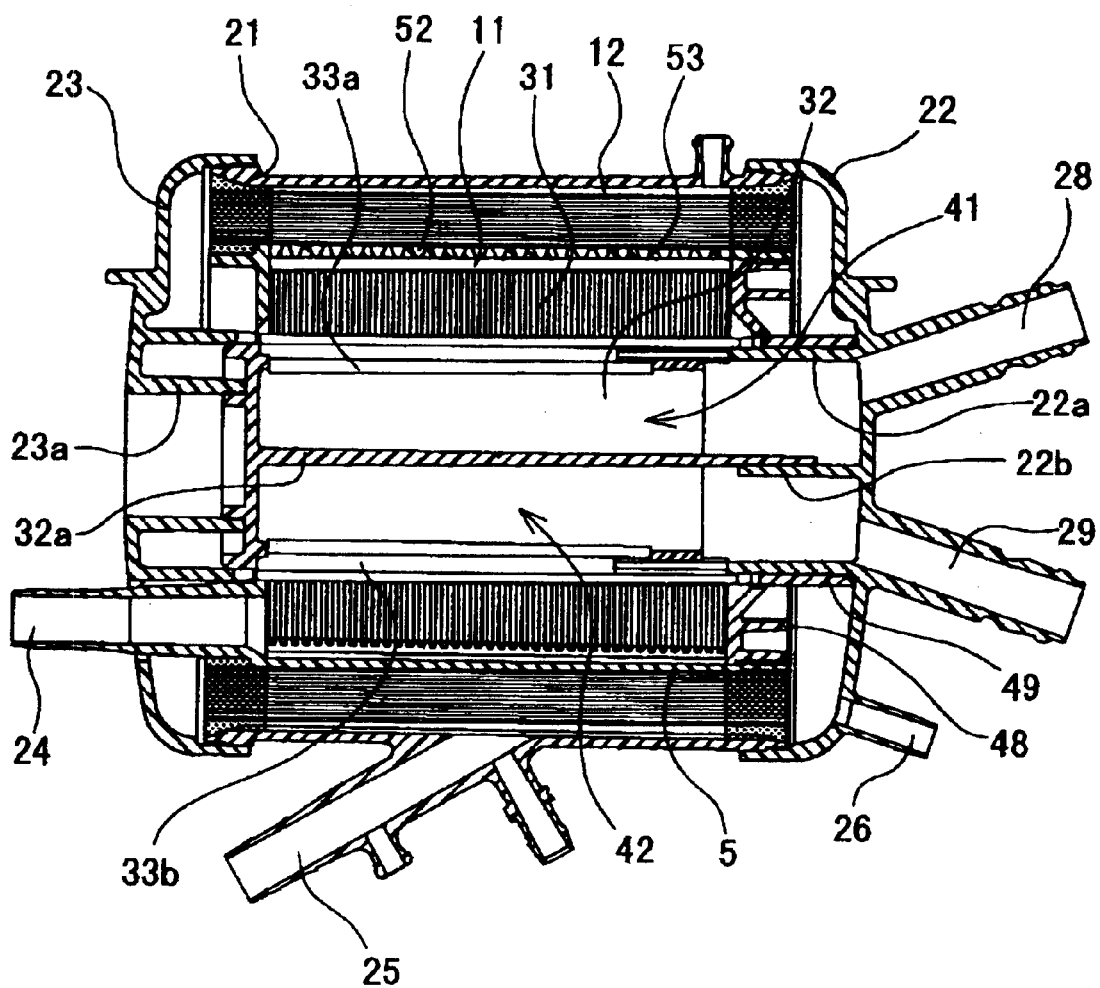
FIG. 11 is a sectional view taken along a line B—B of FIG. 2.

As shown in FIGS. 1 through 4 and FIGS. 10 through 12, the housing 2 includes the cylindrical body 21 having the blood outlet port 25; a first header 22 having a gas inlet port 26, a heating medium inlet port 28, and a heating medium outlet port 29; and a second header 23 having a gas outlet port 27 and an insertion hole of the blood inlet port 24 formed on the cylindrical core 5. Formed on the inner surface of the first header 22 are a cylindrically projected heating medium chamber-forming member connection portion 22a and a partitioning portion 22b dividing the interior of the heating medium chamber-forming member connection portion 22a into two parts. A cylindrically projected heating medium chamber-forming connection portion 23a is formed on the inner surface of the second header 23. Thus, as shown in FIG. 11, the cylindrical heating medium chamber-forming member 32 which will be described later is held by the first header 22 at its one end which is open and held by the second header 23 at its other side which is closed.

Initially, the oxygenating portion will be described below.

Figure 13:
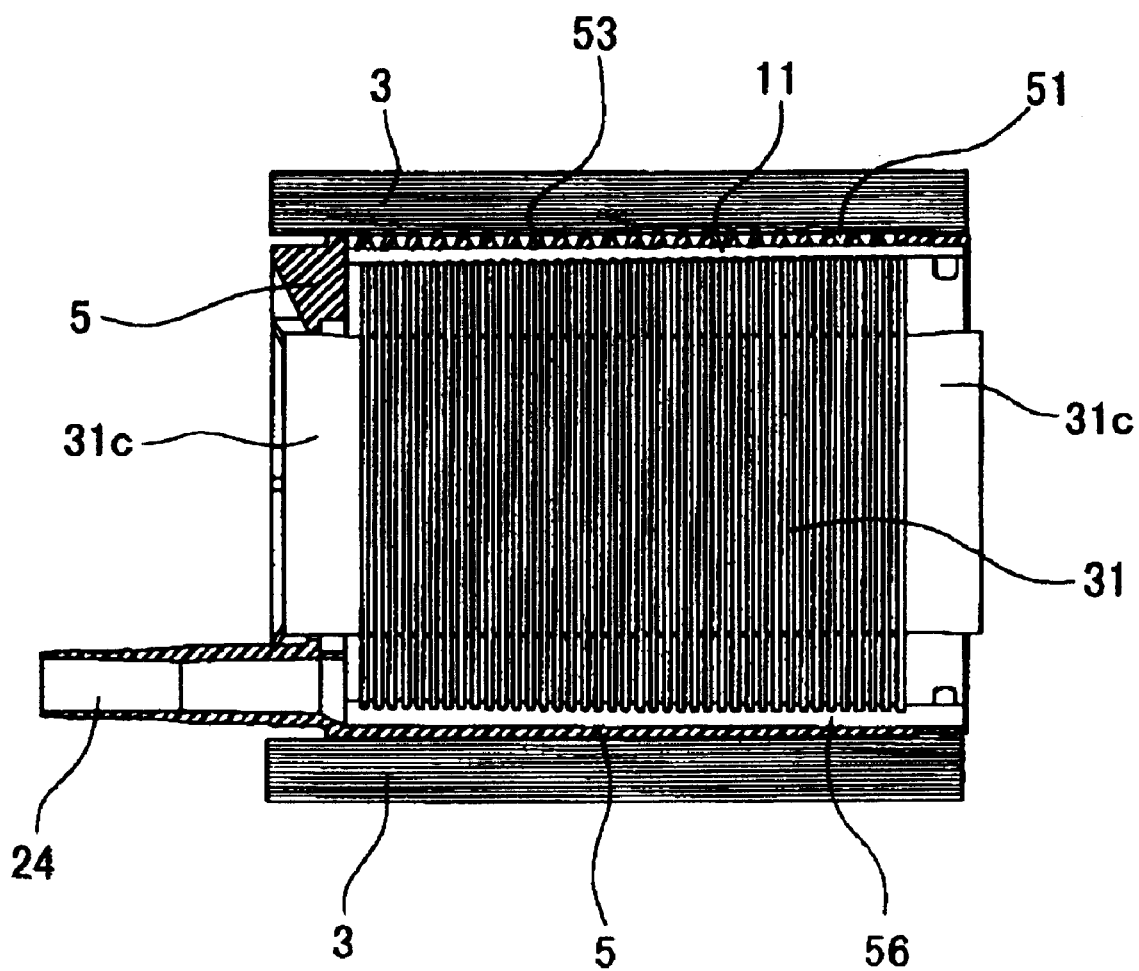
FIG. 13 is an explanatory view for explaining the internal construction of an oxygenating portion of the oxygenator of hollow fiber membrane type according to an embodiment of the present invention.
Figure 14:
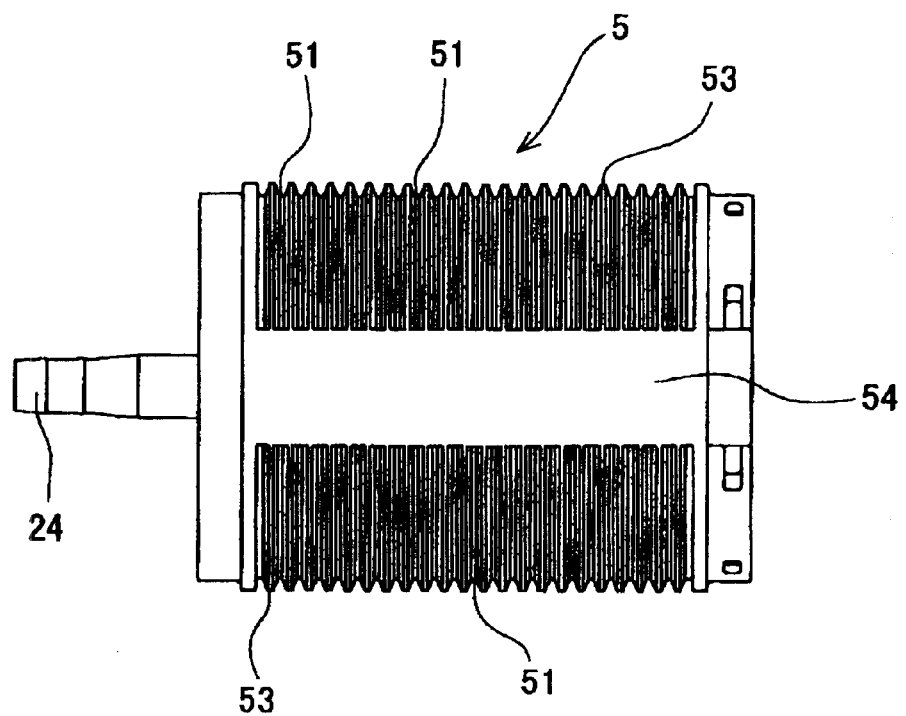
FIG. 14 is a front view showing a cylindrical core for the use of the oxygenator of hollow fiber membrane type according to an embodiment of the present invention.
Figure 15:
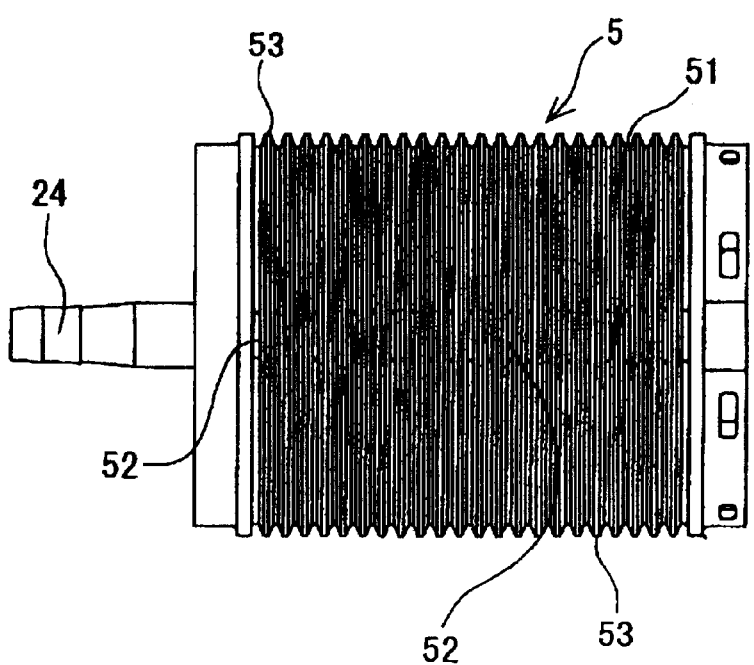
FIG. 15 is a plan view showing the cylindrical core shown in FIG. 14.
Figure 16:
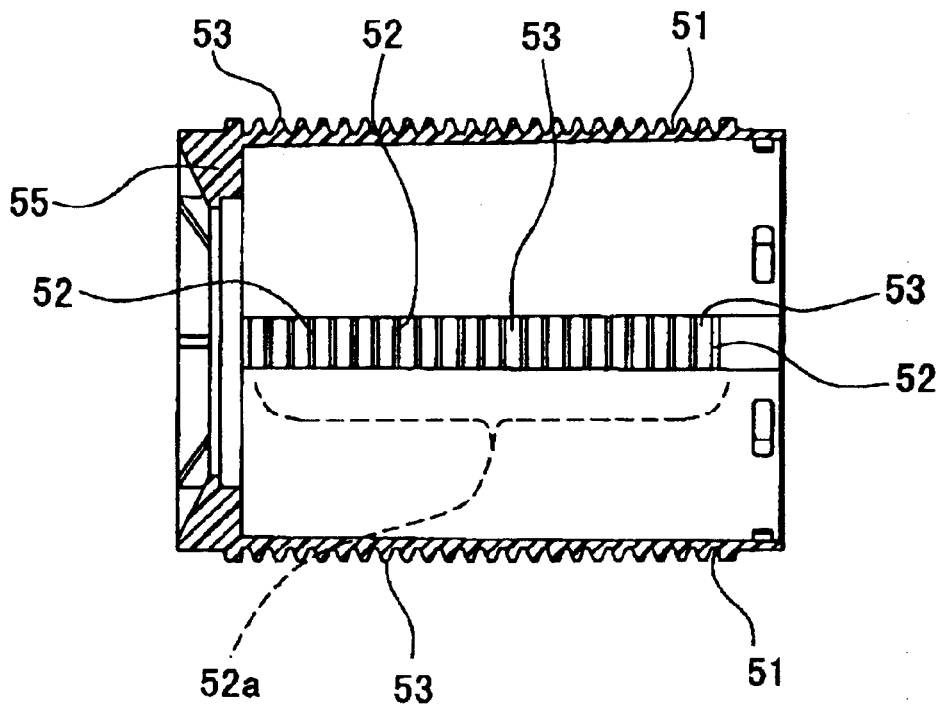
FIG. 16 is a sectional view showing the cylindrical core shown in FIG. 14.

FIG. 13 is an explanatory view for explaining the internal construction of an oxygenating portion of the oxygenator of hollow fiber membrane type according to an embodiment of the present invention. FIG. 14 is a front view showing a cylindrical core for the use of the oxygenator of hollow fiber membrane type according to an embodiment of the present invention. FIG. 15 is a plan view showing the cylindrical core shown in FIG. 14. FIG. 16 is a sectional view showing the cylindrical core shown in FIG. 14.

Figure 17:
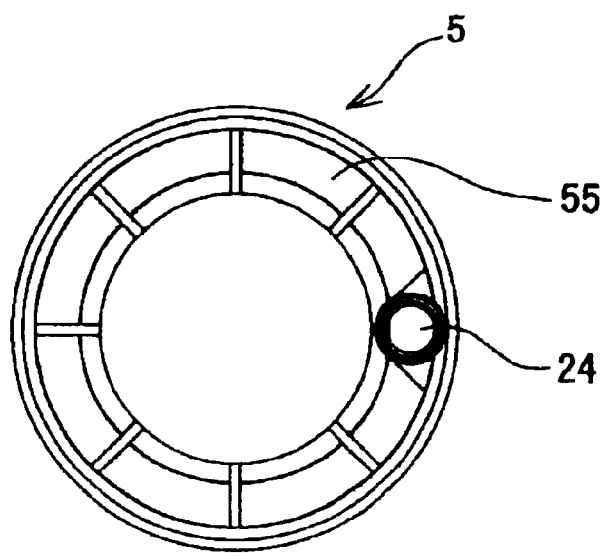
FIG. 17 is a left side view showing the cylindrical core shown in FIG. 14.
Figure 18:
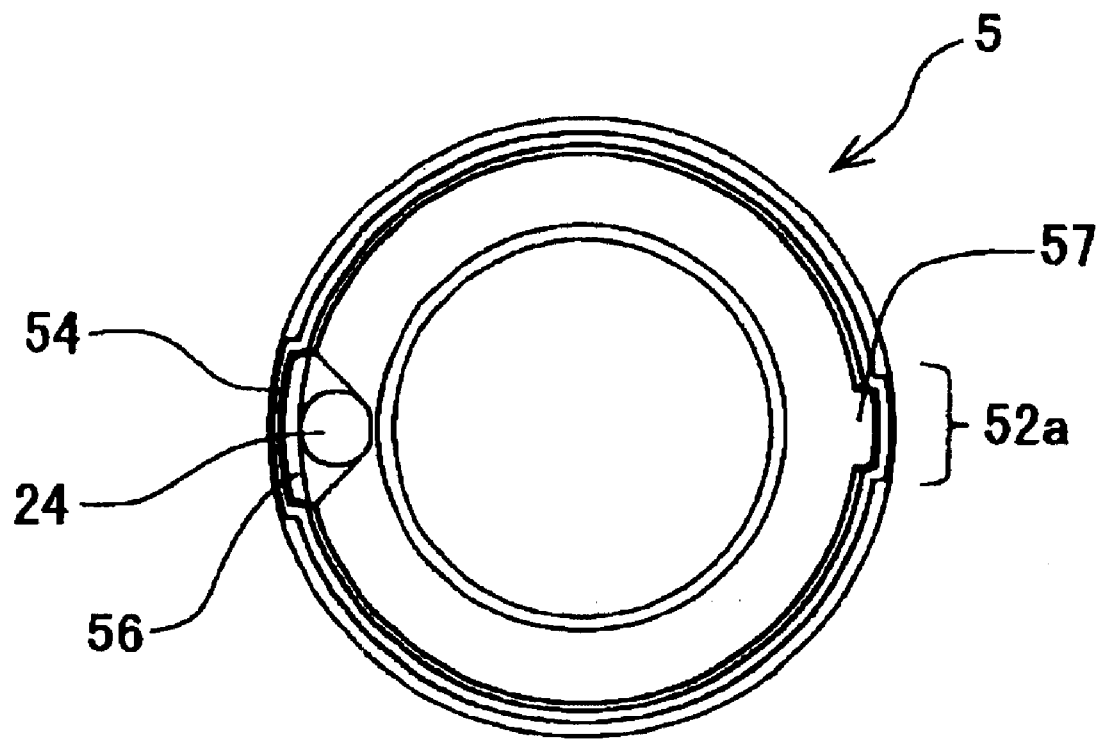
FIG. 18 is a right side view showing the cylindrical core shown in FIG. 14.

FIG. 17 is a left side view showing the cylindrical core shown in FIG. 14. FIG. 18 is a right side view showing the cylindrical core shown in FIG. 14.

The oxygenating portion has the cylindrical core 5 and the cylindrical hollow fiber membrane bundle 3 consisting of a plurality of the hollow fiber membranes 3a wound on the outer surface of the cylindrical core 5.

As shown in FIGS. 4, 10 through 18, at one end of the cylindrical core 5, the cylindrical core 5 has a doughnut-shaped projection 55 having a predetermined width and extending inward. The blood inlet port 24 is formed on the outer surface of a flat portion of the doughnut-shaped projection 55 such that the blood inlet port 24 projects outward in parallel with the axis of the cylindrical core 5.

Formed on the outer surface of the cylindrical core 5 is a plurality of grooves 51 forming the blood duct between the outer surface of the cylindrical core 5 and the inner surface of the cylindrical hollow fiber membrane bundle 3. The cylindrical core 5 has the blood-circulating openings 52 allowing the communication between the groove 51 and the first blood chamber 11 formed between the cylindrical core 5 and the cylindrical heat exchanging part (in other word, the first blood chamber 11 is formed inside the cylindrical core 5). It is preferable that the outer diameter of the cylindrical core is in the range of 20–100 mm and that the effective length thereof (length thereof not embedded in partitioning wall) is in the range of 100–730 mm.

The oxygenator 1 has a first blood chamber formed inside the cylindrical core and communicating to the blood inlet portion and a second blood chamber formed between said housing and an outer surface of the hollow fiber membrane bundle and communicating to the blood outlet portion. The cylindrical core is a plurality of grooves forming a blood duct between an outer surface of the cylindrical core and an inner surface of the cylindrical hollow fiber membrane bundle and blood-circulating openings communicating the groove to said first blood chamber More specifically, except both ends thereof, the cylindrical core 5 has a plurality of uncontinuous grooves 51 parallel with one another and annular ribs 53 formed between the adjacent grooves 51. The groove 51 of the cylindrical core 5 is formed in almost the entirety of a portion (effective length, portion not embedded in partitioning wall) which contributes to exchange of gas in the cylindrical hollow fiber membrane bundle. The cylindrical core 5 which is used in the embodiment has an ungrooved portion (groove unformed portion) 54 located at a position on approximately the extension of the blood inlet port 24 and having a flat surface and extending on almost the entirety of the portion forming the groove 51 of the cylindrical core 5. Therefore, the groove 51 of the cylindrical core 5 is an annular groove (circular arc-shaped groove) having a start portion and an end portion, and the rib 53 of the cylindrical core 5 is an annular rib 53 having a start portion and an end portion. Because the cylindrical core 5 has the ungrooved portion 54 having the flat surface and extending on almost the entirety of the portion forming the groove 51 of the cylindrical core 5, the stability of the configuration of the cylindrical hollow fiber membrane bundle 3 formed on the outer surface of the cylindrical core 5 can be improved. However, the ungrooved portion 54 is not necessarily formed. The groove 51 and the rib 53 of the cylindrical core 5 may be endless, namely, completely annular. The depth of the groove 51 is favorably in the range of 0.5–10.0 mm and more favorably in the range of 2.0–4.0 mm. The pitch of the groove 51 is favorably in the range of 1.0–10.0 mm and more favorably in the range of 3.0–5.0 mm. The width (width of largest portion) is favorably in the range of 1.0–10.0 mm and more favorably in the range of 2.0–4.0 mm. Because the cylindrical core 5 has a plurality of the grooves 51 formed in almost all of the entirety of the effective length (portion not embedded in partitioning wall) of the hollow fiber membrane bundle 3, it is possible to disperse blood in almost all of the entirety of the hollow fiber membrane bundle 3 and effectively utilize the entire hollow fiber membrane bundle 3. Thus, the cylindrical core 5 has a high degree of gas exchange performance.

It is preferable that the apex of a mountain portion (rib 53) formed between the adjacent ribs 51 of the cylindrical core 5 is formed as a flat surface. The width of the flat surface of the rib 53 is favorably in the range of 0.1 to 5.0 mm and more favorably in the range of 0.8 to 1.2 mm. Because the apex of the rib 53 is formed as a flat surface, the stability of the configuration of the cylindrical hollow fiber membrane bundle 3 formed on the outer surface of the cylindrical core 5 can be improved. In section, the groove 51 is wider (for example, trapezoidal in section) toward the apex of the rib 53. Because the groove 51 becomes wider toward the inner surface of the hollow fiber membrane bundle, the groove 51 allows blood to be introduced into the hollow fiber membrane bundle smoothly.

The blood inlet port 24 is formed at one-end side of the cylindrical core 5. The blood-circulating opening 52 is formed in a region confronting a region which is formed along an extended line of the axial line of the blood inlet port 24. This construction allows uniform circulation of blood in the first blood chamber 11 formed between the cylindrical core and the cylindrical heat exchanging part and high efficiency of heat exchange performance. More specifically, as shown in FIGS. 12 and 18, the cylindrical core 5 has an ungrooved portion 54 formed along the extended line of blood inlet 24 and extending in almost the entirely of a grooved-formed part. Because the ungrooved portion 54 is thin, it is possible to form a blood guide portion 56 inside the cylindrical core 5, with the blood guide portion 56 disposed on the extended line of the blood inlet port 24. The inner diameter of the blood guide portion 56 is larger than those of the other portions of the groove-formed part. The blood guide portion 56 allows blood to axially flow through the entire first blood chamber 11 formed between the cylindrical core and the cylindrical heat exchanging part.

The blood-circulating opening 52 is formed in a region (position) confronting the ungrooved portion 54 (blood guide portion 56). In the cylindrical core 5, the blood-circulating opening 52 consists of a plurality of openings communicating with the annular grooves 51. That is, the blood-circulating opening 52 is formed by recessing the groove 51 of the cylindrical core 5 at a position thereof confronting the ungrooved portion 54 (blood guide portion). Thus, the rib 53 is formed between the adjacent blood-circulating openings 52. In the cylindrical core 5, the thickness of the rib 53 is small in a portion thereof located in an opening-formed portion 52a. As shown in FIG. 18, the inner diameter of the opening-formed portion 52a is larger than that of the inner diameters of the other portions of the groove-formed part, similarly to the ungrooved portion 54 (blood guide portion) to form a second blood guide portion 57 therein. As described above, owing to the formation of the mountain consisting of the rib 53 formed in the opening-formed portion 52a, it is possible to prevent the deterioration of the performance of the cylindrical core 5. Further, owing to the contact between the rib 53 and the hollow fiber membrane 3a, it is possible to allow the hollow fiber membrane bundle 3 to maintain its original shape. Further, the opening-formed portion 52a is formed as the thin portion by making the inner diameter thereof larger than the other portions of the groove-formed part. Thus, it is possible to securely guide blood which has flowed through the first blood chamber 11 to the opening-formed portion 52a In addition to the above-described construction, the oxygenator of hollow fiber membrane type may have following construction. For example, instead of the mountain consisting of the rib 53, the opening-formed portion 52a may have one blood-circulating opening communicating with all of the annular grooves 51 or have a plurality of blood-circulating openings communicating with a plurality of the annular grooves 51.

Figure 4:
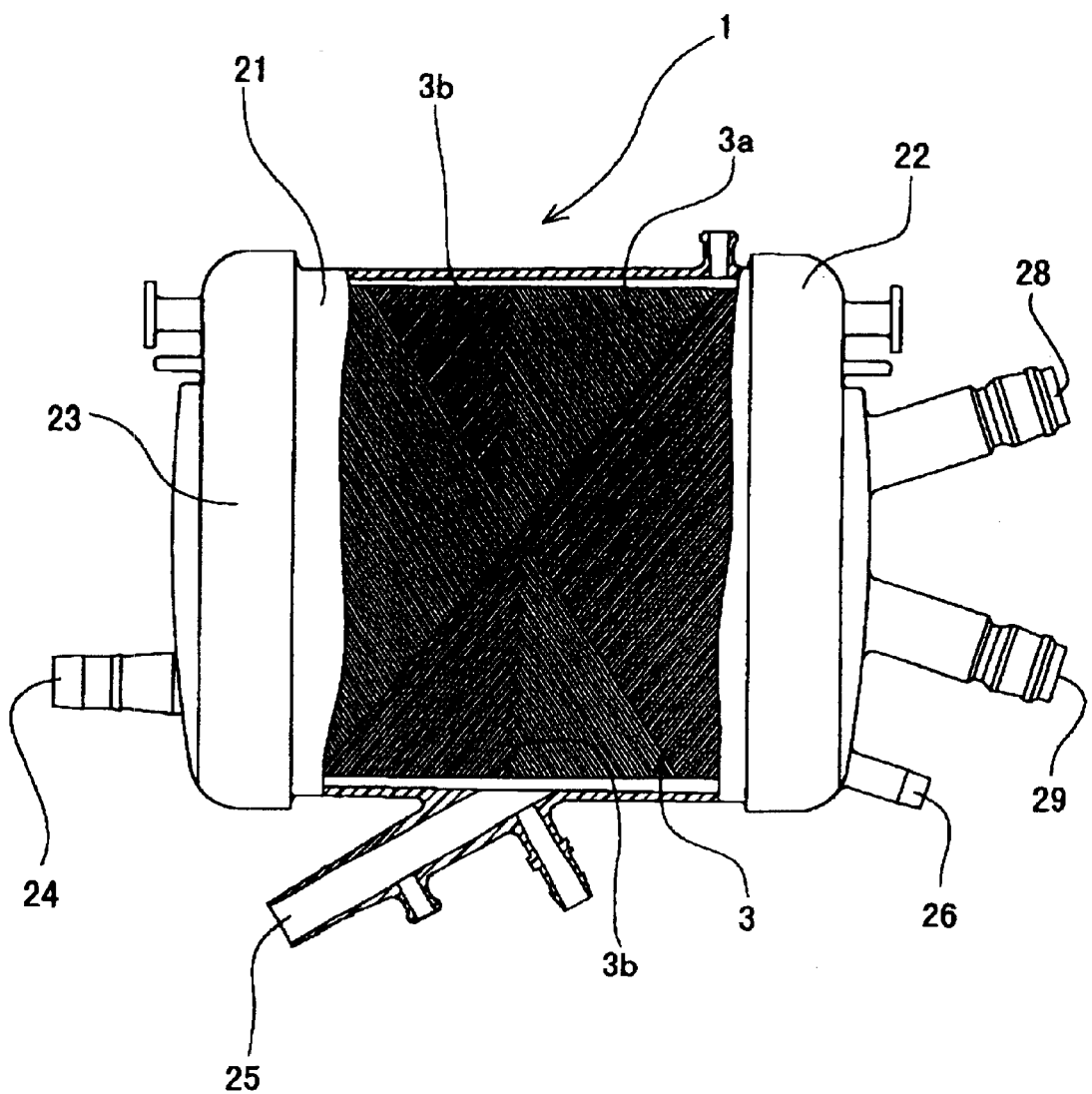
FIG. 4 is an explanatory view showing a state in which a part of a housing of the oxygenator of hollow fiber membrane type shown in FIG. 1 is partly removed.

The hollow fiber membrane bundle 3 is wound on the outer surface of the cylindrical core 5. As shown in FIG. 4, by sequentially winding the hollow fiber membranes 3a forming the hollow fiber membrane bundle 3 on the cylindrical core 5, the hollow fiber membranes 3a are multi-layered, in other words, spirally layered on the outer surface of the cylindrical core 5. That is, the hollow fiber membranes 3a are reeled on the cylindrical core 5. In the neighborhood of the center of the cylindrical core in its longitudinal direction, the hollow fiber membrane layer has cross portions 3b (cross winding portion, hereinafter referred to as cross portion 3b) of the hollow fiber membranes 3a. The positions of the cross portions 3b are differentiated from one another, depending on a portion of each hollow fiber membrane layer. As shown in FIG. 4, by changing the positions of the cross portions, it is possible to prevent contact of the cross portions of two layers laminated on each other. Thus, it is possible to prevent generation of a short-circuited path of blood. The cross portions are continuously formed by winding two to six hollow fiber membranes on the cylindrical core 5 such that adjacent winds of the hollow fiber membranes cross each other.

Figure 5:
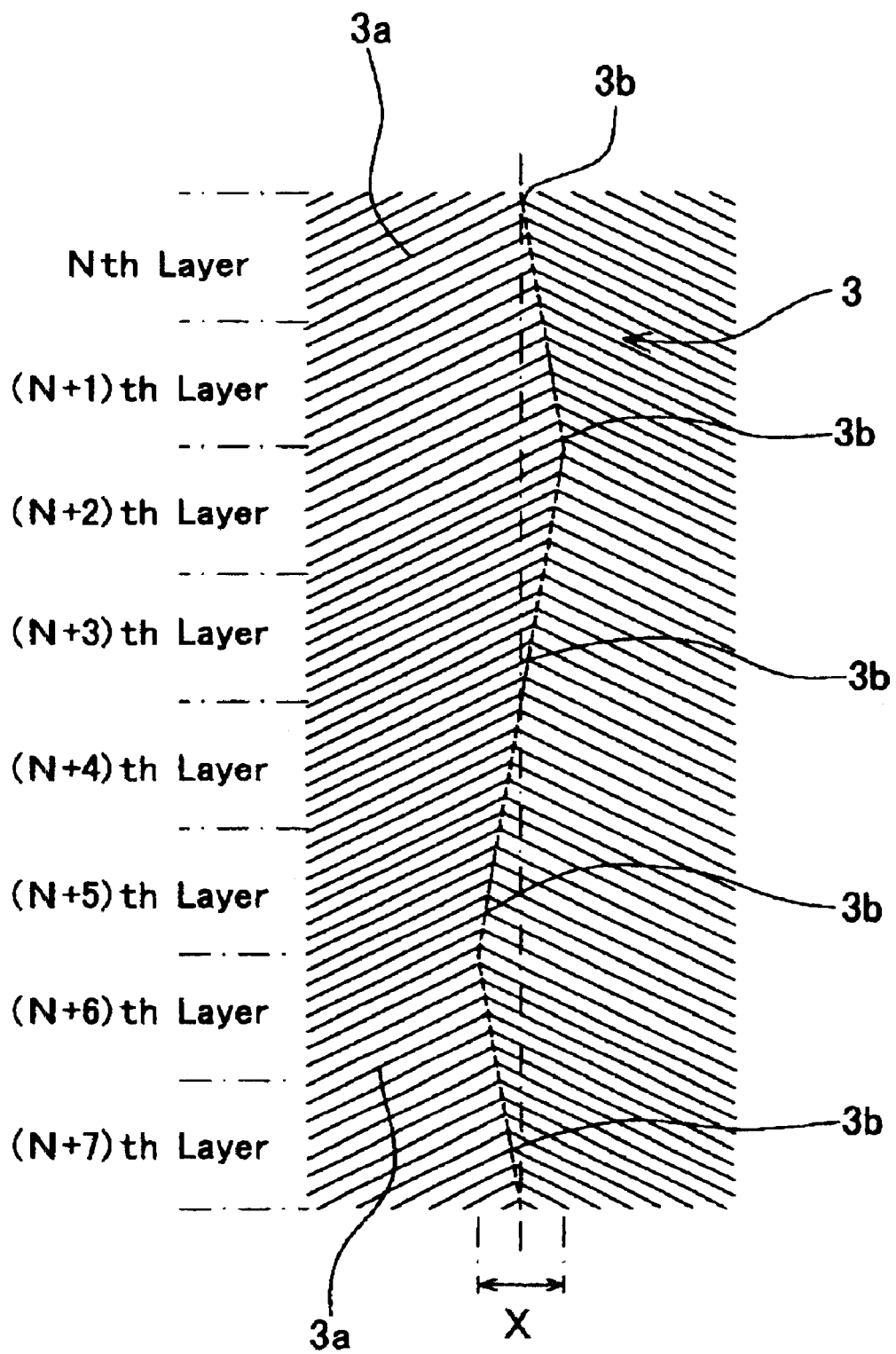
FIG. 5 is an explanatory view showing an example of a cross portion of the hollow fiber membrane bundle for the use of the oxygenator of hollow fiber membrane type of the present invention.

In the example shown in FIG. 4, the positions of the cross portions 3b are differentiated from one another, depending on portions of each hollow fiber membrane layer to prevent contact of cross portions 3b of two layers laminated on each other. In other words, the cross portion of a first layer and a second layer not adjacent to the first layer may be coincident with each other in the longitudinal direction of the hollow fiber membrane bundle through the cross portion (in other words, hollow fiber membrane layer) of a third layer whose cross portion does not contact that of the first layer or that of the second layer. More specifically, as shown in FIG. 5 showing a developed state of the hollow fiber membrane bundle (layer of hollow fiber membrane), the position of the cross portion 3b is continuously changed with respect to the center of the hollow fiber membrane bundle in its longitudinal direction. Each layer shown in FIG. 5 shows a hollow fiber membrane layer of the hollow fiber membrane bundle wound around the cylindrical core 5. The hollow fiber membrane layers are laminated one upon another such that an (N+1)th layer is laminated on an Nth layer and so on. In the example shown in FIG. 5, the position of the cross portion 3b is continuously changed such that eight layers consisting of the Nth layer through an (N+7)th layer form one set. The entire hollow fiber membrane bundle is composed of a plurality of sets each consisting of eight layers. The number of sets of the hollow fiber membrane layers is generally 3–40, although it depends on the area of a film of the oxygenator. The number of the hollow fiber membrane layers is generally 3–40.

In the example shown in FIG. 5, at the start position of the Nth layer, the cross portion 3b is disposed at the center of the hollow fiber membrane bundle in its longitudinal direction. Then the cross portion 3b shifts toward one end (right side) of the hollow fiber membrane bundle in its longitudinal direction gradually. At the termination (in other words, start position of an (N+2)th layer) of the (N+1)th layer, the cross portion 3b is disposed at the one end (right side) of the hollow fiber membrane bundle in its longitudinal direction. Then, the cross portion 3b shifts toward the center of the hollow fiber membrane bundle in its longitudinal direction again. At the termination (in other words, the start position of an (N+4)th layer) of an (N+3)th layer, the cross portion 3b is disposed at the center of the hollow fiber membrane bundle in its longitudinal direction, as in the case of the cross portion 3b disposed at the start position in the Nth layer.

The cross portion at the start position of the Nth layer and the cross portion at the start of the (N+4)th layer are coincident with each other in the longitudinal direction of the hollow fiber membrane bundle via the (N+1)th layer, the (N+2)th layer, and the (N+3)th layer, but do not contact each other. Then, the cross portion shifts toward the other side (left side) of the hollow fiber membrane bundle. At the termination (in other words, the start position of an (N+6)th layer) of an (N+5)th layer, the cross portion 3b is disposed at the other end (left side) of the hollow fiber membrane bundle in its longitudinal direction. Then, the cross portion 3b shifts toward the center of the hollow fiber membrane bundle in its longitudinal direction.

At the termination of an (N+7)th layer, the cross portion 3b is disposed at the center of the hollow fiber membrane bundle in its longitudinal direction, as in the case of the cross portion 3b disposed at the start position in the Nth layer. The cross portion at the start position of the (N+4)th layer and the cross portion at the termination (in other words, the start position of the Nth layer) of the (N+7)th layer are coincident with each other in the longitudinal direction of the hollow fiber membrane bundle via the (N+5)th layer, (N+6)th layer, and the (N+7)th layer, but do not do not contact each other.

Figure 6:
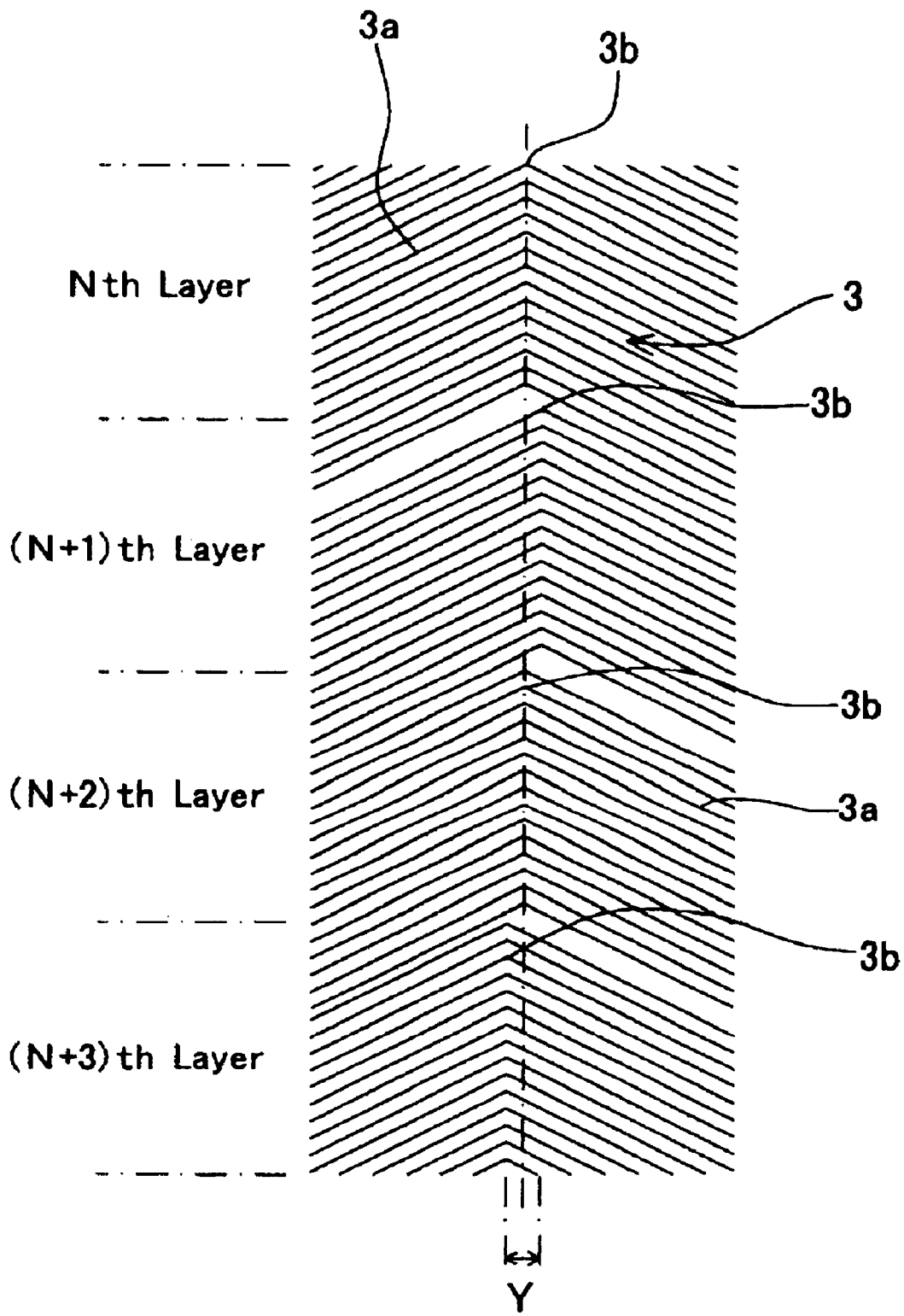
FIG. 6 is an explanatory view showing another example of a cross portion of the hollow fiber membrane bundle for the use of the oxygenator of hollow fiber membrane type of the present invention.

As shown in FIG. 6, the position of the cross portion 3b of the hollow fiber membrane bundle 3 may shift stepwise. More specifically, as shown in FIG. 6 indicating a developed state of the hollow fiber membrane bundle, the position of the cross portion 3b changes stepwise with respect to the center of the hollow fiber membrane bundle in its longitudinal direction. Each layer shown in FIG. 6 shows a hollow fiber membrane layer of the hollow fiber membrane bundle which is wound around the cylindrical core 5. The (n+1)th layer of the hollow fiber membrane is wound on the nth layer and so on. In the example shown in FIG. 6, the hollow fiber membrane layers are laminated one upon another such that the (N+1)th layer is laminated on the Nth layer and so on. In the example shown in FIG. 6, the positions of the cross portion 3b is continuously changed such that four layers consisting of the Nth layer through the (N+3)th layer form one set. The entire hollow fiber membrane bundle is composed of a plurality of sets each consisting of four layers. The number of sets of the hollow fiber membrane layers is generally 3–40, although it depends on the area of a film of the oxygenator. The number of the hollow fiber membrane layers is generally 3–40.

In the example shown in FIG. 6, in the Nth layer, the cross portion 3b is disposed at the center of the hollow fiber membrane bundle in its longitudinal direction. In the (N+1)th layer, the cross portion 3b shifts toward one end (right side) of the hollow fiber membrane bundle in its longitudinal direction. In the (N+2)th layer, the cross portion 3b is disposed at the center of the hollow fiber membrane bundle in its longitudinal direction again. Then, in the (N+3)th layer, the cross portion 3b shifts toward the other end (left side) of the hollow fiber membrane bundle in its longitudinal direction. In the Nth layer, the cross portion 3b shifts toward the center of the hollow fiber membrane bundle in its longitudinal direction again. The cross portion of the nth layer and that of the (N+2)th layer are coincident each other in the longitudinal direction of the hollow fiber membrane bundle through the (N+1)th layer interposed therebetween, but do not contact each other.

In the above-described examples, the cross portions never contact each other. It is preferable that the cross portions are formed in this manner. However, the cross portion may be so formed that depending on a portion of the hollow fiber membrane layer, positions of the cross portions are differentiated from one another to prevent contact between the cross portion of another layer and the cross portions of two layers laminated on each other.

Figure 7:
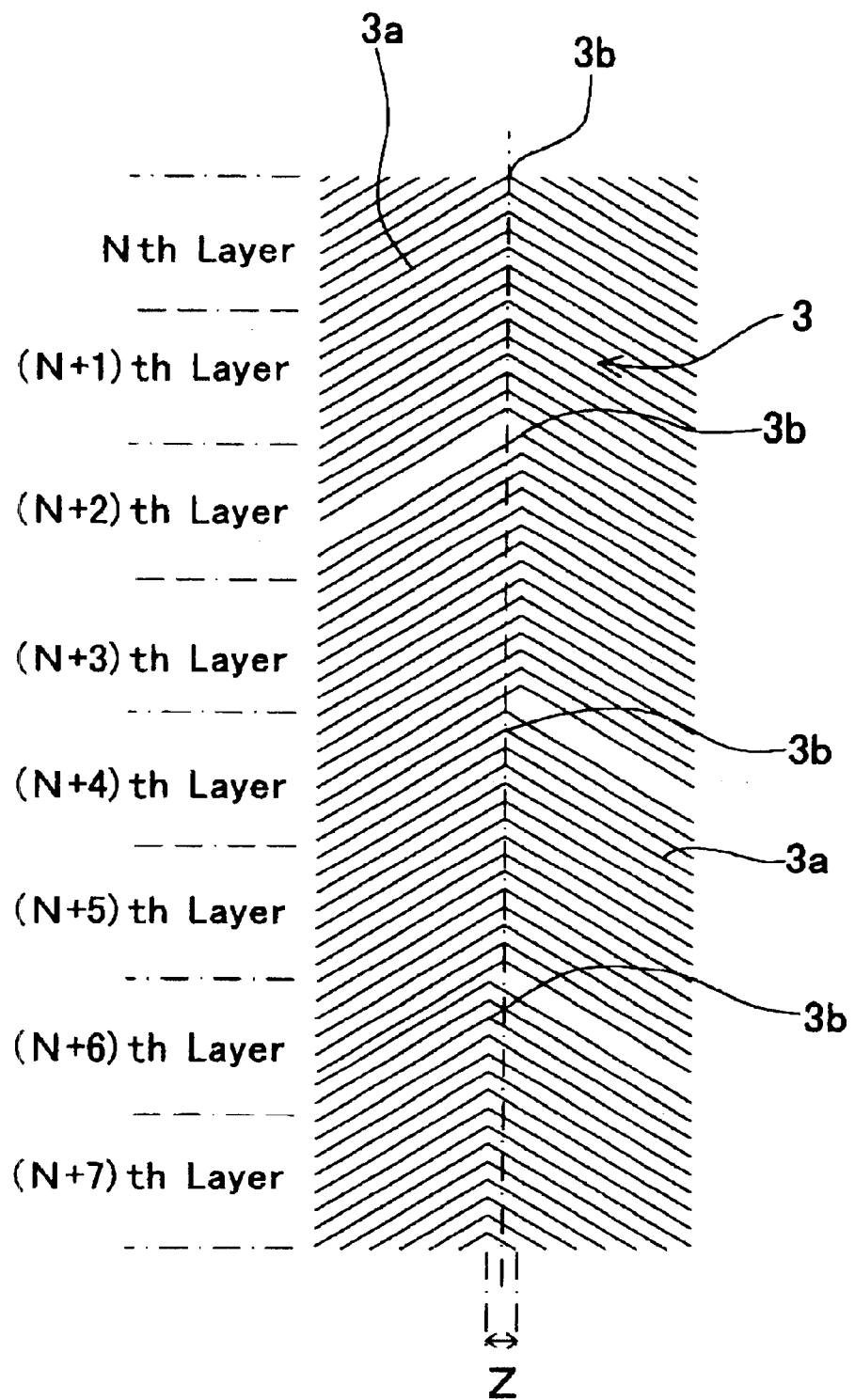
FIG. 7 is an explanatory view showing still another example of a cross portion of the hollow fiber membrane bundle for the use of the oxygenator of hollow fiber membrane type of the present invention.

More specifically, in the example shown in FIG. 7, the cross portion of a second layer (upper layer) is in contact with that of a first layer (lower layer) which is in contact with the second layer (upper layer). However, depending on a portion of each hollow fiber membrane layer, the positions of the cross portions 3b are differentiated from one another to prevent the cross portion of a third layer laminated on the second layer from making contact with the cross portion of the second layer. However, the cross portion of each of the first and second layers may be coincident with that of the third layer in the longitudinal direction of the hollow fiber membrane bundle through a fourth layer interposed between the second layer and the third layer. More specifically, as shown in FIG. 7 indicating a developed state of the hollow fiber membrane bundle, the position of the cross portion 3b changes stepwise with respect to the center of the hollow fiber membrane bundle in its longitudinal direction. Each layer shown in FIG. 7 shows a hollow fiber membrane layer of the hollow fiber membrane bundle which is wound around the cylindrical core 5. The (n+1)th layer of the hollow fiber membrane is wound on the nth layer and so on. In the example shown in FIG. 7, the hollow fiber membrane layers are laminated one upon another such that the (N+1)th layer is laminated on the Nth layer and so on. In the example shown in FIG. 7, the position of the cross portion 3b is continuously changed such that eight layers consisting of the Nth layer through the (N+7)th layer form one set. The entire hollow fiber membrane bundle is composed of a plurality of sets each consisting of eight layers. The number of sets of the hollow fiber membrane layers is generally 3–40, although it depends on the area of a film of the oxygenator. The number of the hollow fiber membrane layers is generally 3–40.

In the example shown in FIG. 7, in the Nth layer and the (N+1)th layer, the cross portion 3b is disposed at the center the hollow fiber membrane bundle in its longitudinal direction. Thus, the cross portion 3b of the nth layer and that of the (N+1)th layer laminated on the nth layer contact each other. In the (N+2)th layer and the (N+3)th layer, the cross portions 3b shift to one end (right side) of the hollow fiber membrane bundle in its longitudinal direction. In the (N+4)th layer and the (N+5)th layer, the cross portions 3b shift to the center of the hollow fiber membrane bundle in its longitudinal direction again. In the (N+6)th layer and the (N+7)th layer, the cross portions 3b shift to the other end (left side) of the hollow fiber membrane bundle in its longitudinal direction. In the Nth layer, the cross portion 3b shifts to the center of the hollow fiber membrane bundle in its longitudinal direction again. That is, the cross portions of the two layers in contact with each other contact each other. However, the cross portion of the layer in contact with one of the two layers does not contact the cross portion of the two layers. The cross portion of the nth layer and that of the (N+1)th layer are coincident with that of the (N+4)th layer and that of the (N+5)th layer in the longitudinal direction of the hollow fiber membrane bundle through the (N+2)th layer and the (N+3)th layer, but do not contact each other.

In the examples shown in FIGS. 5 through 7, all the cross portions are disposed favorably within a width of 80 mm (X of FIG. 5, Y of FIG. 6, and Z of FIG. 7) and more favorably within a width of 60 mm with respect to the center of the cylindrical core in its longitudinal direction. In other words, the largest interval between the cross portions of the cylindrical core in its longitudinal direction is favorably in the range of 3mm–80 mm and more favorably in the range of 4–60 mm. The width (X of FIG. 5, Y of FIG. 6, and Z of FIG. 7), namely, the largest interval between the cross portions is favorably in the range of 2%–75% and more favorably in the range of 3–50% of the length of the hollow fiber membrane bundle in its longitudinal direction.

The hollow fiber membrane bundle is formed of one or a plurality of hollow fiber membranes spaced at regular intervals wound simultaneously on the cylindrical core 5. It is preferable that the distance between the adjacent hollow fiber membranes is in the range of $\frac{1}{10}$–$\frac{1}{1}$ of the outer diameter thereof.

As described above, the hollow fiber membrane bundle in which the position of the cross portion shifts is formed by winding one or a plurality of hollow fiber membranes simultaneously and spirally on a cylindrical core with adjacent hollow fiber membranes spaced at substantially regular intervals. In winding the hollow fiber membranes on the cylindrical core, a cylindrical core-rotating means 61 and a winder 62 for weaving the hollow fiber membranes are operated, based on a computation equation (1) shown below and make a continuous relative movement in the range of favorably −40 mm+40 mm, more favorably −30 mm+30 mm, and most favorably −15 mm+15 mm in the axial direction of the cylindrical core supposing that the center of the cylindrical core in its longitudinal direction is 0:

traverse [mm/lot]×n(integer and 2 or more)=traverse width×2+ (outer diameter of fiber+interval between adjacent fibers)×number of fibers to be wound    computation equation (1).

In the relative movement of the cylindrical core-rotating means 61 and the winder 62 in the axial direction of the cylindrical core, any one of the following three patterns can be selected:

(1) The winder moves with the cylindrical core-rotating means fixed.

(2) The cylindrical core-rotating means moves with the winder fixed.

(3) Both the cylindrical core-rotating means and the winder move.

The above n of the equation (1) expressing the relationship between the number of rotations of the winding rotary member and the number of reciprocations of the winder should be in the range of 2–5. It is preferable that n is 2. In the case where an integer is selected as n of the equation (1), one cross portion (cross-winding portion) of the hollow fiber membrane is formed in the neighborhood of the center of the hollow fiber membrane bundle in its longitudinal direction. In the oxygenator 1 of the embodiment, 2 is selected as n of the equation (1). In this case, the cross portion 3b is formed in the neighborhood of the center of the hollow fiber membrane bundle 3 (before both ends are cut) in its longitudinal direction, with the hollow fiber membrane bundle 3 wound around the outer surface of the cylindrical core 5.

A hollow fiber membrane bundle forming device 60 shown in FIG. 8 will be described below. The hollow fiber membrane bundle forming device 60 is so constructed that a cylindrical core-rotating means 61 is stationary and only a winder 62 moves to allow the relative movement of the cylindrical core-rotating means 61 and the winder 62 in the axial direction of the core.

The hollow fiber membrane bundle forming device 60 has the cylindrical core-rotating means 61 and the winder 62. The cylindrical core-rotating means 61 has a motor 63, a motor shaft 64, and a core-installing member 65 fixed to the motor shaft 64. The cylindrical core 5 is installed on the core-installing member 65 and rotated by the motor 63.

Figure 8:
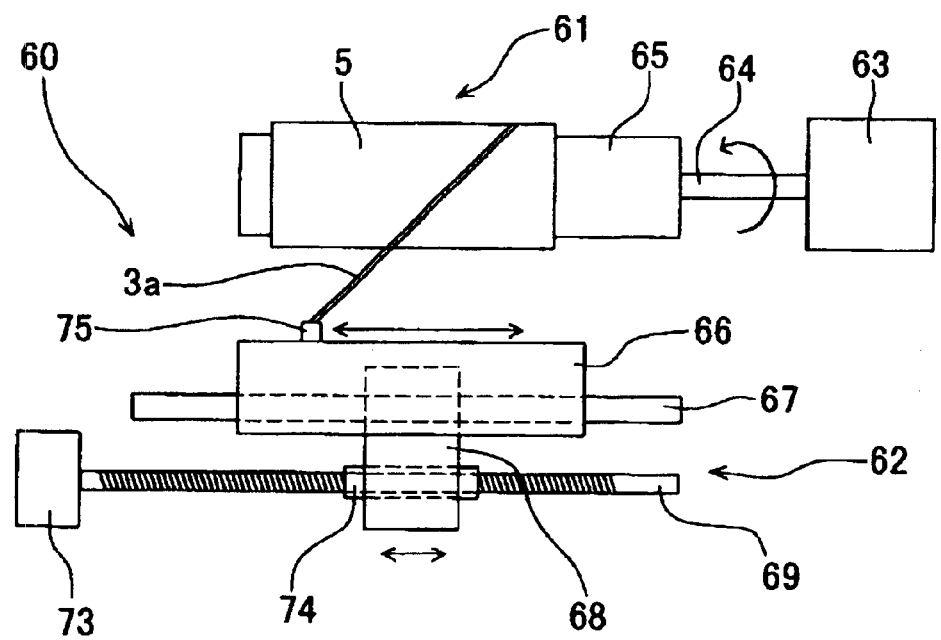
FIG. 8 is an explanatory view showing an example of a hollow fiber membrane bundle forming device for the use of the oxygenator of hollow fiber membrane type of the present invention.

The winder 62 has a body 66 having a hollow fiber membrane accommodation portion therein and a discharge portion 75 discharging the hollow fiber membrane and moving in the axial direction (parallel with the axis of the cylindrical core, namely, the direction shown with the arrow of FIG. 8) of the body 66. The body 66 is fixed to a linear table 68 moving along a linear rail 67 and to a ball nut member 74. A motor 73 drives a ball screw shaft 69 to rotate it. As a result, the ball nut member 74 moves in the direction shown with the arrow to allow the body 66 to move in the direction shown with the arrow. The motor 73 is rotatable forward and rearward. The rotational direction of the motor 73 is adjusted by a controller not shown in FIG. 8.

According to the hollow fiber membrane bundle forming device 60, the traverse width is fixed by the movement width of the discharge portion 75, but the traverse position can be changed by moving the body 66 and the discharge portion 75. Thereby, the position of the cross portion of the hollow fiber membrane can be changed.

A hollow fiber membrane bundle forming device 70 shown in FIG. 9 will be described below. The hollow fiber membrane bundle forming device 70 is so constructed that a winder 72 is stationary and a cylindrical core-rotating means 71 moves to allow the relative movement of the cylindrical core-rotating means 71 and the winder 72 in the axial direction of the core.

The hollow fiber membrane bundle forming device 70 has the cylindrical core-rotating means 71 and the winder 72.

The cylindrical core-rotating means 71 has a motor 63, a motor shaft 64, and a core-installing member 65 fixed to the motor shaft 64. The cylindrical core 5 is installed on the core-installing member 65 and rotated by the motor 63. The motor 63 is fixed to a linear table 78 moving along a linear rail 77 and to a ball nut member 81. A motor 80 drives a ball screw shaft 79 to rotate it. As a result, the ball nut member 81 moves in the direction shown with the arrow to allow the cylindrical core-rotating means 71 to move in the direction shown with the arrow. The motor 80 is rotatable forward and rearward. The rotational direction of the motor 80 is adjusted by a controller not shown in FIG. 9.

Figure 9:
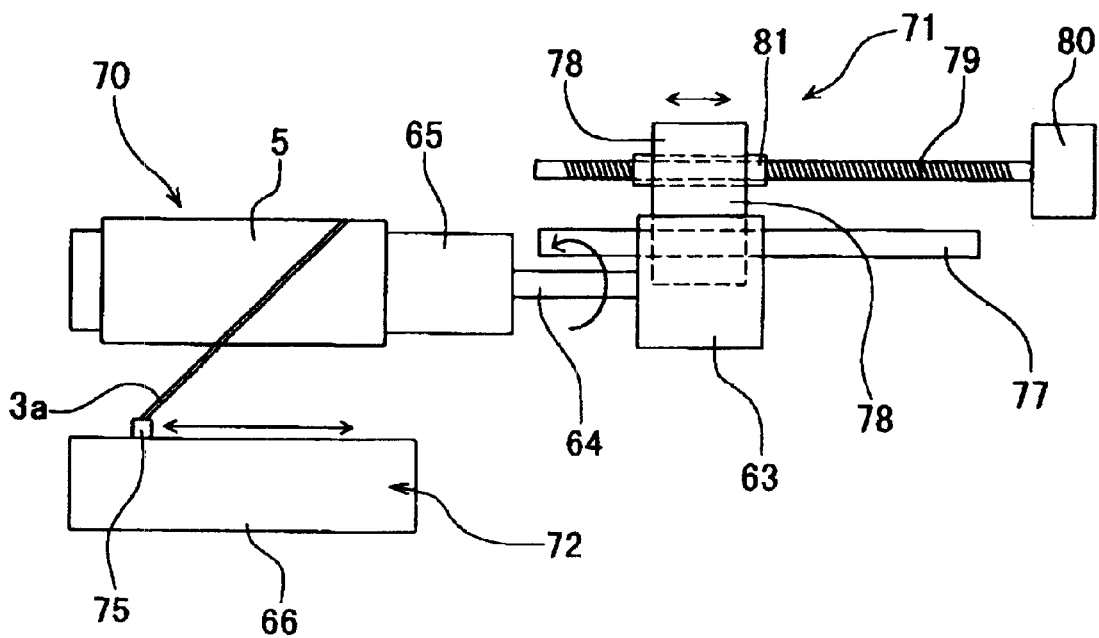
FIG. 9 is an explanatory view showing another example of a hollow fiber membrane bundle forming device for the use of the oxygenator of hollow fiber membrane type of the present invention.

The winder 72 has a body 66 having a hollow fiber membrane accommodation portion therein and a discharge portion 75 discharging the hollow fiber membrane and moving in the axial direction (parallel with the axis of the cylindrical core, namely, the direction shown with the arrow of FIG. 9) of the body 66. According to the hollow fiber membrane bundle forming device 70, the traverse width is fixed by the movement width of the discharge portion 75, but the traverse position can be changed by moving the cylindrical core-rotating means 71 and the discharge portion 75. Thereby, the position of the cross portion of the hollow fiber membrane can be changed.

It is preferable that one or a plurality of the hollow fiber membrane is wound on the cylindrical core 5, with the hollow fiber membranes substantially disposed in parallel with one another and with adjacent ones spaced at substantially regular intervals. Thereby, it is possible to prevent nonuniform flow of blood. It is preferable that the distance between the adjacent hollow fiber membranes is in the range of $\frac{1}{10}$–$\frac{1}{1}$ of the outer diameter thereof. That is, the distance between the adjacent hollow fiber membranes is favorably in the range of 30 $\mu$m–200 $\mu$m and more favorably in the range of 50 $\mu$m –180 cm.

Preferably, the hollow fiber membrane is wound on the outer surface of the cylindrical core 5 in such a manner that the hollow fiber membrane is not disposed on the groove 51 of the cylindrical core 5. In other words, preferably, the hollow fiber membrane is wound spirally along the periphery of the apex of the rib 53 such that the hollow fiber membrane connects the apexes of the rib 53 to each other. In this case, to prevent the hollow fiber membrane from dropping to the groove 51 of the cylindrical core 5, it is preferable to wind the hollow fiber membrane at a predetermined angle relative to the groove 51 (rib 53). More specifically, it is favorable to wind the hollow fiber membrane on the groove 51 at an angle of 10–50 degrees relative to the groove 51 (rib 53) of the cylindrical core 5 and more favorable at an angle of 20–40 degrees relative thereto. By winding the hollow fiber membrane on the groove 51 (rib 53) of the cylindrical core 5 at the predetermined angle relative to the groove 51, foam which cuts into the space between the cylindrical core 5 and the hollow fiber membrane in priming time can be preferably eliminated. Thus, it is possible to improve priming performance, gas exchange performance, and reduce variation in the performance of the cylindrical core 5 because the hollow fiber membrane hardly drops from the cylindrical core 5.

As the hollow fiber membrane, a porous gas exchange film is used. The inner diameter of the porous hollow fiber membrane is preferably in the range of 100–1000 $\mu$m. The thickness thereof is favorably in the range of 5–200 $\mu$m and more favorably in the range of 10–100 $\mu$m. The porosity thereof is favorably in the range of 20–80% and more favorably in the range of 30–60%. The diameter of a pore is favorably in the range of 0.01–54 $\mu$m and more favorably in the range of 0.01–1 $\mu$m. As the material for the porous film, the following hydrophobic macromolecular materials can be used: polypropylene, polyethylene, polysulfone, polyacrylonitrile, polytetrafluoroethylene, cellulose acetate, and the like. Resins of the polyolefin family is favorable. Polypropylene can be most favorable of the resins of the polyolefin family. It is preferable to form pores on the wall of the hollow fiber membrane by drawing method or solid phase-liquid phase separation method. Preferably, the outer diameter of the hollow fiber membrane bundle 3 is in the range of 30–162 mm. Preferably, the thickness of the hollow fiber membrane bundle 3 is in the range of 3 mm–28 mm. It is favorable that the charge percentage of the hollow fiber membrane of the cylindrical hollow fiber membrane bundle 3 formed on the outer surface of the cylindrical core 5 to the cylindrical space formed between the outer and inner surfaces of the cylindrical hollow fiber membrane bundle 3 is in the range of 50–75% and more favorable in the range of 53–73%.

After the hollow fiber membrane bundle is wound on the cylindrical core 5, both ends thereof are cut, with the hollow fiber membrane bundle 3 fixed to the cylindrical body 21 of the housing 2 by means of partitioning walls 8, 9. In the hollow fiber membrane bundle formed by the above-described hollow fiber membrane bundle forming device, because traverse positions are different from one another depending on layers, both ends of the hollow fiber membrane bundle 3 are not coincident with each other. Therefore, it is necessary to cut the formed hollow fiber membrane bundle at a position where all layers of the hollow fiber membranes are laminated one upon another. Unless both ends of the formed hollow fiber membrane bundle are cut at a position where all layers of the hollow fiber membranes are laminated one upon another, the ends of the hollow fiber membrane are not open.

Both ends of the cylindrical core 5 on which the hollow fiber membrane bundle 3 has been wound are liquid-tightly fixed to both ends of the cylindrical body 21 by means of the partitioning walls 8, 9 to form the second blood chamber 12 as an annular space (cylindrical space) between the outer surface of the cylindrical hollow fiber membrane and the inner surface of the cylindrical body 21. The blood outlet port 25 formed on a side surface of the cylindrical body 21 of the housing 2 communicates with the second blood chamber 12. The partitioning walls 8, 9 are formed of a potting agent such as polyurethane, silicone rubber or the like.

As shown in FIG. 13, the cylindrical heat exchanging part which will be described later is accommodated inside the cylindrical core 5 of the oxygenating portion formed as described above. The annular first blood chamber 11 is formed between the cylindrical core 5 and the cylindrical heat exchanging part. The blood inlet port 24 communicates with the first blood chamber 11.

As shown in FIGS. 10 through 12, the cylindrical heat exchanging part includes a cylindrical heat exchanger 31; a cylindrical heating medium chamber-forming member 32 accommodated in the cylindrical heat exchanger 31; and prevention portions 34, 35, for preventing deformation of the heat exchanger, inserted between the cylindrical heat exchanger 31 and the cylindrical heating medium chamber-forming member 32.

The cylindrical heat exchanger 31 of bellows type is used in the embodiment. As shown in FIG. 13, the cylindrical heat exchanger 31 of bellows type includes a bellows-forming portion having a plurality of hollow annular projections formed in substantially parallel with one another on the central side surface thereof and a cylindrical portion 31c formed at both ends of the bellows-forming portion and having an inner diameter substantially equal to that of the bellows-forming portion. One of the two cylindrical portions 31c of the cylindrical heat exchanger 31 is held between the inner surface of the end, of the cylindrical core 5, at the side of the blood inlet port 24 and the second header 23, whereas the other cylindrical portion 31c of the cylindrical heat exchanger 31 is held between the first header 22 and the cylindrical heat exchanger-fixing member 49 inserted between a ring-shaped heat exchange member-fixing member 48 and the first header 22.

The cylindrical heat exchanger 31 of bellows type is made of metal such as stainless steel, aluminum or the like or a resinous material such as polyethylene, polycarbonate or the like. The cylindrical heat exchanger 31 has the shape of a bellows having a short pitch between convexities and concavities. In consideration of strength and heat exchange efficiency, metal such as stainless steel, aluminum or the like is more favorable than the resinous material. The cylindrical heat exchanger 31 is composed of a bellows pipe having many convexities and concavities substantially perpendicular to the axial direction thereof. The difference in distance between a valley and a mountain is favorably in the range of 5.0–20.0 mm and more favorably in the range of 9.0–15.0 mm. The axial length of the cylindrical heat exchanging part is in the range of 100–730 mm, although it is different depending on a patient.

As shown in FIGS. 10 through 12, the cylindrical heating medium chamber-forming member 32 is open at its one end (at the side of the first header 22). The cylindrical heating medium chamber-forming member 32 includes a partitioning wall 32a partitioning the interior thereof into an inlet-side heating medium chamber 41 and an outlet-side heating medium chamber 42; a first opening 33a communicating with the inlet-side heating medium chamber 41 and extending axially; a second opening 33b communicating with the outlet-side heating medium chamber 42 and extending axially; and projections 36a, 36b formed at a position of a side surface thereof forming about 90 degrees with respect to the first opening 33a and the second opening 33b. The projections 36a, 36b confront each other and project outward. The projection 36a penetrates into a groove formed at the center of the inner surface of the prevention portion 34 for preventing deformation of the heat exchanger, thus preventing the movement of the prevention portion 34. Similarly, the projection 36b penetrates into a groove formed at the center of the inner surface of the prevention portion 35, thus preventing the movement of the prevention portion 35.

Referring to FIG. 11, when the open end of the cylindrical heating medium chamber-forming member 32 is fitted on a cylindrical connection portion 22a of the first header 22, a partitioning portion 22b dividing the interior of the cylindrical connection portion 22a contacts one surface (lower surface in the embodiment) of the front portion of a partitioning wall 32a of the cylindrical heating medium chamber-forming member 32. Thereby, the inlet side heating medium chamber 41 inside the cylindrical heating medium chamber-forming member 32 communicates with the heating medium inlet port 28, and the outlet side heating medium chamber 42 communicates with the heating medium outlet port 29.

Each of the prevention portions 34, 35 for preventing deformation of the heat exchanger has a notch extending axially at an end thereof. As shown in FIG. 12, a medium inlet side duct passage 37 and a medium outlet side duct passage 38 are formed by contacting the prevention portions 34 and 35 with each other. The prevention portions 34 and 35 may be formed integrally.

With reference to FIGS. 10 through 12, the flow of the heating medium in the heat exchanger of the oxygenator 1 of the embodiment will be described below. The heating medium which has flowed into the oxygenator from the heating medium inlet port 28 flows into the inlet side heating medium chamber 41 through the interior of the first header 22. Then, the heating medium flows between the cylindrical heat exchanger 31 and the prevention portions 34, 35 through the medium inlet side duct passage 37 defined by the inlet side first opening 33a of the cylindrical heating medium chamber-forming member 32 and the contact portion of the prevention portions 34, 35. Meantime, the heating medium heats or cools the cylindrical heat exchanger 31. Then, the heating medium passes through the medium outlet side duct passage 38 defined by the contact portion of the prevention portions 34, 35 and the outlet side second opening 33b of the cylindrical heating medium chamber-forming member 32, thus flowing into the outlet side heating medium chamber 42 inside the cylindrical heating medium chamber-forming member 32. Then, the heating medium passes through the interior of the first header 22 and flows out from the heating medium outlet port 29.

In the oxygenator 1, blood which has flowed thereinto from the blood inlet port 24 flows into the blood guide portion 56 constituting a part of the first blood chamber 11 disposed between the cylindrical core 5 and the cylindrical heat exchanging part. After the blood flows between the cylindrical core 5 and the cylindrical heat exchanging part, it passes through the blood-circulating opening 52 formed at the position confronting the blood guide portion 56 and flows out from the cylindrical core 5. Then, the blood flows into the grooves 51 formed between the outer surface of the cylindrical core 5 and the inner surface of the cylindrical hollow fiber membrane bundle 3 and flows into the hollow fiber membrane. In the oxygenator of the embodiment, because a large number of the grooves 51 are formed in almost all of the entirety of the portion (effective length, portion not embedded in partitioning wall) which contributes to exchange of gas in the cylindrical hollow fiber membrane bundle 3, it is possible to disperse blood in almost all of the entirety of the hollow fiber membrane bundle 3 and to effectively utilize the entire hollow fiber membrane bundle 3. Thus, the cylindrical core 5 has a high degree of gas exchange performance. After the blood contacts the hollow fiber membrane and a gas exchanged is performed, the blood flows into the second blood chamber 12 formed between the cylindrical body 21 of the housing 2 and the outer surface of the hollow fiber membrane and then flows out from the blood outlet port 25. A gas containing oxygen which has flowed into the oxygenator from the gas inlet port 26 passes through the first header 22 and flows into the hollow fiber membrane from an end surface of the partitioning wall. Then, the blood passes through the second header 23 and flows out from the gas outlet port 27.

Except the material of the heat exchanger 31, as the material of the cylindrical body 21 of the housing 2, the cylindrical core 5, the first header 22, the second header 23, and other members, polyolefin (for example, polyethylene, polypropylene), ester resin (for example, polyethylene terephthalate), styrene resin (for example, polystyrene, MS resin, MBS resin), and polycarbonate.

It is preferable that the blood contact surface of the oxygenator 1 is formed as an antithombic surface. The antithombic surface can be formed by applying and fixing an antithrombin to the blood contact surface. Heparin, urokinase, HEMA-St-HEMA copolymer, and poly-HEMA can be used as the antithrombins.

EXAMPLES

Examples and comparison examples of the oxygenator of hollow fiber membrane type of the present invention will be described below.

Examples

The outer diameter, inner diameter, and length of the cylindrical body of the housing used in the example were 110 mm, 106 mm, and 114 mm, respectively. The first and second headers used in the example had a shape as shown in FIGS. 1 through 4.

In the heat exchanger of bellows type used in the example, the outer diameter, the inner diameter, the length, the length of the bellows-forming portion, the number of mountains, and the pitch of the bellows (mountain) were 75 mm, 50 mm, 114 mm, 90.0 mm, 40, and 2.25 mm, respectively. An assembly of a one end-closed cylindrical heating medium chamber-forming member having a shape as shown in FIG. 11 and two members for preventing deformation of the heat exchanger installed thereon was inserted into the heat exchanger of bellows type. In the cylindrical heating medium chamber-forming member, the outer diameter of the cylindrical portion, the outer diameter of the rib portion, and the length were 39.0 mm, 47.0 mm, and 114.0 mm, respectively. In the two members for preventing deformation of the heat exchanger, the length and the length of the largest-diameter portion were 92.0 mm and 52.0 mm, respectively. The member for preventing deformation of the heat exchanger had 40 ribs (height: 1.0 mm, width: 0.5 mm) formed in parallel with one another on its outer surface. The assembly of the cylindrical heating medium chamber-forming member and the members for preventing deformation of the heat exchanger was inserted into the heat exchanger such that the rib of the member for preventing deformation of the heat exchanger penetrated into the space at the inner side of the valley of the heat exchanger of bellows type.

In the cylindrical core used in the example, the length, the outer diameter, the inner diameter, the length of the groove-forming portion, the depth of the groove, the interval between adjacent grooves, and the width of the flat surface at the apex of the rib were 114.0 mm, 84 mm, 75.0 mm, 90.0 mm, 2.5 mm, 3.0 mm, and 1.0 mm, respectively. The cylindrical core had 40 grooves on its outer surface. The heat exchanger of bellows type was inserted into the cylindrical core.

Four hollow fiber membranes made of porous polypropylene were rewound on the outer surface of the cylindrical core with the four hollow fiber membranes spaced at regular intervals of 100 μm. The inner diameter, the outer diameter, and the porosity of each hollow fiber membrane were 195 μm, 295 μm, and about 35%, respectively. The subsequent four hollow fiber membranes were wound on the outer surface of the cylindrical core with the four hollow fiber membranes spaced at the same intervals as that of the previous ones. In this manner, a hollow fiber membrane bobbin containing a heat exchanger having a duct restriction plate was prepared. In winding the hollow fiber membrane on the cylindrical core, the cylindrical core-rotating member and the winder for weaving the hollow fiber membrane are operated, based on the equation shown below. In this embodiment, 2 is selected as n of the equation. The winder was moved continuously in a small amount. That is, the width of the cross portion was changed within ±2.5 mm to compose one set of eight layers. The hollow fiber membrane bundle obtained in this manner had 12 sets, 18 layers, and a charge percentage of 68.

traverse [mm/lot]×n(integer and 2 or more)=traverse width× 2±(outer diameter of fiber+interval between adjacent fibers)× number of fibers to be wound Both ends of the hollow fiber membrane bundle and the cylindrical core were fixed to both ends of the cylindrical body of the housing with a potting agent. Then, while the cylindrical core was being rotated around the heat exchanging part, both ends of the hollow fiber membrane bobbin was cut without cutting the heat exchanging part. The first header and the second header were installed on both ends of the cylindrical body of the housing. In this manner, an oxygenator of hollow fiber membrane type as shown in FIGS. 1 through 4 and 10 through 12 was prepared. The film area and blood charge amount of the oxygenator were 2.5 m$^2$ and 250 ml, respectively.

Comparison Example

An oxygenator of hollow fiber membrane type having a film area of 2.5 m$^2$ and a blood charge amount of 250 ml was prepared by a method similar to that of the example, except that the winder was not moved axially in forming the hollow fiber membrane bundle on the outer surface of the cylindrical core.

Experiment

By using cattle blood, experiments were conducted on the oxygenator of the example and that of the comparison example thus prepared. The cattle blood used in the experiments was standard venous blood established by AAMI (Association for the Advance of Medical Instrumentation). The anticoagulant added venous blood was circulated in each oxygenator at a flow rate of 7L/min. Blood was collected from each oxygenator in the neighborhood of the blood inlet port and the blood outlet port to find the movement amount of oxygen and that of carbon dioxide by finding the partial pressure of oxygen gas, the partial pressure of carbon dioxide gas, and pH with a blood gas analyzer. The pressure loss was also measured at the flow rate of 7L/min. The results are as shown in table 1 shown below.

TABLE 1

|  | movement amount of oxygen (L/min) | movement amount of carbon dioxide (L/min) | pressure loss (Pa) |
| --- | --- | --- | --- |
| Example | 447.6 | 310.3 | 11066 |
| Comparison example | 356.5 | 220.5 | 11999 |

According to the oxygenator of the present invention, it is rare that cross portion-caused short-circuited path of blood is generated in the hollow fiber membrane bundle and possible to provide a high degree of gas exchange function.

What is claimed is:

1. An oxygenator of hollow fiber membrane type comprising a cylindrical core; a cylindrical hollow fiber membrane bundle consisting of a plurality of gas-exchange hollow fiber membranes wound on an outer surface of said cylindrical core; a housing accommodating said cylindrical hollow fiber membrane bundle; a gas inlet portion and a gas outlet portion both communicating with the interior of said hollow fiber membranes; and a blood inlet portion and a blood outlet portion communicating with the outside of said hollow fiber membranes and the interior of said housing, wherein said hollow fiber membranes of said cylindrical hollow fiber membrane bundle are multi-layered on the outer surface of said cylindrical core; each hollow fiber membrane layer has cross portions of the hollow fiber membranes in the neighborhood of a center of said cylindrical core in the longitudinal direction thereof and positions of said cross portions of each of said respective hollow fiber membrane layers are differentiated from one another to prevent contact between said cross portions of said hollow fiber membrane layers laminated on each other or to prevent contact between said cross portion of another hollow fiber membrane layer and cross portions of two hollow fiber membrane layers laminated on each other.

2. An oxygenator of hollow fiber membrane type according to claim 1, wherein a position of said cross portion changes continuously.

3. An oxygenator of hollow fiber membrane type according to claim 1, wherein a positions of said cross portion changes stepwise.

4. An oxygenator of hollow fiber membrane type according to claim 1, wherein a maximum interval between said cross portions is in the range of 2%–75% of a length of said hollow fiber membrane bundle in a longitudinal direction thereof.

5. An oxygenator of hollow fiber membrane type according to claim 1, wherein all of said cross portions are disposed within a width of 80 mm with respect to the center of a cylindrical core in a longitudinal direction thereof.

6. An oxygenator of hollow fiber membrane type according to claim 1, wherein a maximum interval between said cross portions is in the range of 3mm–80 mm.

7. An oxygenator of hollow fiber membrane type according to claim 1, wherein said cross portions are continuously formed by winding two to six hollow fiber membranes in substantially parallel with one another and with adjacent ones spaced at substantially regular intervals on a cylindrical core such that adjacent winds of said hollow fiber membranes cross each other.

8. An oxygenator of hollow fiber membrane type according to claim 1, wherein said oxygenator of hollow fiber membrane type has a cylindrical heat exchanging part accommodated in said cylindrical core.

9. An oxygenator of hollow fiber membrane type according to claim 1, wherein said oxygenator has two partitioning walls for fixing both ends of said cylindrical hollow fiber membrane bundle to said housing; and a gas inlet port and a gas outlet port both communicating with an interior of said hollow fiber membrane.

10. An oxygenator of hollow fiber membrane type according to claim 1, wherein said hollow fiber membrane bundle is formed by winding one or a plurality of hollow fiber membranes simultaneously and spirally on a cylindrical core with adjacent hollow fiber membranes spaced at substantially regular intervals; and in winding said hollow fiber membranes on said cylindrical core, a cylindrical core-rotating means and a winder for weaving said hollow fiber membranes are operated, based on a computation equation (1) shown below and make a continuous relative movement in the range of 40 mm+40 mm in an axial direction of said cylindrical core supposing that the center of said cylindrical core in a longitudinal direction thereof is 0:

traverse [mm/lot]×n(integer and 2 or more)=traverse width× 2±(outer diameter of fiber+interval between adjacent fibers× number of fibers to be wound       computation equation (1).

11. An oxygenator of hollow fiber membrane type according to claim 10, wherein in the relative movement of said cylindrical core-rotating means and said winder in the axial direction of said cylindrical core, said winder moves with said cylindrical core-rotating means fixed or said cylindrical core-rotating means moves with said winder fixed.

12. An oxygenator of hollow fiber membrane type according to claim 1, wherein said oxygenator has a first blood chamber formed inside the cylindrical core and communicating to the blood inlet portion and a second blood chamber formed between said housing and an outer surface of the hollow fiber membrane bundle and communicating to the blood outlet portion, and said cylindrical core is a plurality of grooves forming a blood duct between an outer surface of the cylindrical core and an inner surface of the cylindrical hollow fiber membrane bundle and blood-circulating openings communicating the groove to said first blood chamber.

13. An oxygenator of hollow fiber membrane type according to claim 1, wherein said cylindrical core has a plurality of circular arc-shaped grooves substantially parallel with one another and a ungrooved portion having a flat surface and extending on almost the entirety of a portion forming said grooves of the cylindrical core.

* * * * *

UNITED STATES PATENT AND TRADEMARK OFFICE
CERTIFICATE OF CORRECTION

PATENT NO.   : 6,503,451 B2                                        Page 1 of 1
DATED        : January 7, 2003
INVENTOR(S)  : Tomohiko Ikeda et al.

It is certified that error appears in the above-identified patent and that said Letters Patent is hereby corrected as shown below:

<u>Column 11,</u>
Line 67, "-54" is changed to -- -5 --.

Signed and Sealed this

Twenty-eighth Day of October, 2003

JAMES E. ROGAN
*Director of the United States Patent and Trademark Office*